US012611253B2

(12) United States Patent
Cook et al.

(10) Patent No.: US 12,611,253 B2
(45) Date of Patent: Apr. 28, 2026

(54) OPTICAL ANALYZER ASSEMBLY AND METHOD FOR INTRAVASCULAR LITHOTRIPSY DEVICE

(71) Applicant: Boston Scientific Scimed Inc., Maple Grove, MN (US)

(72) Inventors: Christopher A. Cook, Laguna Niguel, CA (US); Eric Schultheis, San Clemente, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 161 days.

(21) Appl. No.: 17/172,980

(22) Filed: Feb. 10, 2021

(65) Prior Publication Data

US 2021/0290286 A1    Sep. 23, 2021

Related U.S. Application Data

(60) Provisional application No. 62/991,394, filed on Mar. 18, 2020.

(51) Int. Cl.
*A61B 18/20* (2006.01)
*A61B 18/04* (2006.01)
(Continued)

(52) U.S. Cl.
CPC .......... *A61B 18/245* (2013.01); *A61B 18/042* (2013.01); *A61B 18/26* (2013.01);
(Continued)

(58) Field of Classification Search
None
See application file for complete search history.

(56) References Cited

U.S. PATENT DOCUMENTS

| | | | |
|---|---|---|---|
| 4,649,924 A | 3/1987 | Taccardi | |
| 4,699,147 A | 10/1987 | Chilson et al. | |

(Continued)

FOREIGN PATENT DOCUMENTS

| | | |
|---|---|---|
| AU | 2017205323 | 1/2022 |
| AU | 2019452180 | 1/2022 |

(Continued)

OTHER PUBLICATIONS

International Search Report and Written Opinion dated Nov. 8, 2022 in PCT Application Serial No. PCTUS/2022/039678.
(Continued)

*Primary Examiner* — Lynsey C Eiseman
(74) *Attorney, Agent, or Firm* — SEAGER, TUFTE & WICKHEM, LLP

(57) ABSTRACT

A catheter system for treating a treatment site within or adjacent to a vessel wall includes a light source, a balloon, a light guide, and an optical analyzer assembly. The light source generates light energy. The balloon is positionable substantially adjacent to the vascular lesion. The balloon has a balloon wall that defines a balloon interior that receives a balloon fluid. The light guide receives light energy from the light source at a guide proximal end and guides the light energy toward a guide distal end and into the balloon interior. The optical analyzer assembly is configured to optically analyze light energy emitted from the guide proximal end of the light guide.

24 Claims, 2 Drawing Sheets

(51) Int. Cl.
    *A61B 18/24*         (2006.01)
    *A61B 18/26*         (2006.01)
    *A61B 18/00*         (2006.01)
    *A61B 18/22*         (2006.01)

(52) U.S. Cl.
    CPC ................. *A61B 2018/0022* (2013.01); *A61B*
            *2018/00369* (2013.01); *A61B 2018/00386*
            (2013.01); *A61B 2018/2015* (2013.01); *A61B*
            *2018/2035* (2013.01); *A61B 2018/20361*
            (2017.05); *A61B 2018/204* (2013.01); *A61B*
                                *2018/2288* (2013.01)

(56)                References Cited

U.S. PATENT DOCUMENTS

| | | | |
|---|---|---|---|
| 4,799,479 A | 1/1989 | Spears |
| 4,850,351 A | 7/1989 | Herman |
| 4,913,142 A | 4/1990 | Kittrell et al. |
| 4,932,954 A | 6/1990 | Wondrazek et al. |
| 4,955,895 A | 9/1990 | Suglyama |
| 4,960,108 A | 10/1990 | Reichel et al. |
| 4,994,059 A | 2/1991 | Kosa et al. |
| 4,998,930 A | 3/1991 | Lundahl |
| 5,019,075 A | 5/1991 | Spears et al. |
| 5,034,010 A | 7/1991 | Kittrell et al. |
| 5,041,121 A | 8/1991 | Wondrazek et al. |
| 5,057,106 A | 10/1991 | Kasevich et al. |
| 5,082,343 A | 1/1992 | Coult et al. |
| 5,093,877 A | 3/1992 | Aita et al. |
| 5,104,391 A | 4/1992 | Ingle |
| 5,104,392 A | 4/1992 | Kittrell et al. |
| 5,109,452 A | 4/1992 | Selvin et al. |
| 5,116,227 A | 5/1992 | Levy |
| 5,126,165 A | 6/1992 | Akihama et al. |
| 5,152,768 A | 10/1992 | Bhatta |
| 5,173,049 A | 12/1992 | Levy |
| 5,176,674 A | 1/1993 | Hofmann |
| 5,181,921 A | 1/1993 | Makita et al. |
| 5,188,632 A | 2/1993 | Goldenberg |
| 5,200,838 A | 4/1993 | Nudelman |
| 5,269,777 A | 12/1993 | Doiron |
| 5,290,277 A | 3/1994 | Vercimak et al. |
| 5,324,282 A | 6/1994 | Dodick |
| 5,328,472 A | 7/1994 | Steinke et al. |
| 5,336,184 A | 8/1994 | Teirstein |
| 5,363,458 A | 11/1994 | Pan |
| 5,372,138 A | 12/1994 | Crowley |
| 5,387,225 A | 2/1995 | Euteneur |
| 5,400,428 A | 3/1995 | Grace |
| 5,410,797 A | 5/1995 | Steinke et al. |
| 5,417,689 A | 5/1995 | Fine |
| 5,422,926 A | 6/1995 | Smith |
| 5,431,647 A | 7/1995 | Purcell |
| 5,454,809 A | 10/1995 | Janssen |
| 5,456,680 A | 10/1995 | Taylor |
| 5,474,537 A | 12/1995 | Solar |
| 5,496,311 A | 3/1996 | Abele et al. |
| 5,509,917 A | 4/1996 | Cecchetti |
| 5,519,798 A | 5/1996 | Shahid |
| 5,540,679 A | 7/1996 | Fram |
| 5,562,657 A | 10/1996 | Griffin |
| 5,598,494 A | 1/1997 | Behrmann et al. |
| 5,609,606 A | 3/1997 | O'Boyle |
| 5,611,807 A | 3/1997 | O'Boyle |
| 5,637,877 A | 6/1997 | Sinofsky |
| 5,661,829 A | 8/1997 | Zheng |
| 5,697,377 A | 12/1997 | Wittkamph |
| 5,718,241 A | 2/1998 | Ben-Haim et al. |
| 5,729,583 A | 3/1998 | Tang |
| 5,764,843 A | 6/1998 | Macken et al. |
| 5,772,609 A | 6/1998 | Nguyen et al. |
| 5,860,974 A | 1/1999 | Abele |
| 5,891,135 A | 4/1999 | Jackson et al. |
| 5,906,611 A | 5/1999 | Dodick et al. |

| | | | |
|---|---|---|---|
| 5,944,697 A | 8/1999 | Benett et al. |
| 6,007,514 A | 12/1999 | Nita |
| 6,015,404 A * | 1/2000 | Altshuler ............. A61B 18/203 606/9 |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,203,537 B1 | 3/2001 | Adrian |
| 6,210,404 B1 | 4/2001 | Shadduck |
| 6,339,470 B1 | 1/2002 | Papademetriou et al. |
| 6,356,575 B1 | 3/2002 | Fukumoto |
| 6,368,318 B1 | 4/2002 | Visuri et al. |
| 6,423,055 B1 | 7/2002 | Farr |
| 6,500,174 B1 | 12/2002 | Maguire et al. |
| 6,514,203 B2 | 2/2003 | Bukshpan |
| 6,514,249 B1 | 2/2003 | Maguire |
| 6,524,251 B2 | 2/2003 | Rabiner et al. |
| 6,538,739 B1 * | 3/2003 | Visuri .................. G01N 21/431 356/497 |
| 6,544,218 B1 | 4/2003 | Choi |
| 6,548,010 B1 | 4/2003 | Stivland et al. |
| 6,560,387 B1 | 5/2003 | Hehlen et al. |
| 6,607,502 B1 | 8/2003 | Maguire et al. |
| 6,631,220 B1 | 10/2003 | Liang et al. |
| 6,652,547 B2 | 11/2003 | Rabiner et al. |
| 6,666,834 B2 | 12/2003 | Restle et al. |
| 6,702,781 B1 | 3/2004 | Reifart et al. |
| 6,773,447 B2 | 8/2004 | Laguna |
| 6,824,554 B1 | 11/2004 | Jang |
| 6,849,994 B1 | 2/2005 | White et al. |
| 6,890,317 B2 | 5/2005 | Gerdts et al. |
| 6,947,785 B1 | 9/2005 | Beatty et al. |
| 6,966,890 B2 | 11/2005 | Coyle et al. |
| 6,978,168 B2 | 12/2005 | Beatty et al. |
| 6,990,370 B1 | 1/2006 | Beatty et al. |
| 7,273,470 B2 | 9/2007 | Wantink |
| 7,309,324 B2 | 12/2007 | Hayes et al. |
| 7,367,967 B2 | 5/2008 | Eidenschink |
| 7,470,240 B2 | 12/2008 | Schultheiss et al. |
| 7,539,231 B1 | 5/2009 | Honea et al. |
| 7,569,032 B2 | 8/2009 | Naimark et al. |
| 7,599,588 B2 | 10/2009 | Eberle et al. |
| 7,641,646 B2 | 1/2010 | Kennedy, II |
| 7,691,079 B2 | 4/2010 | Gobel |
| 7,713,260 B2 | 5/2010 | Lessard |
| 7,758,572 B2 | 7/2010 | Weber et al. |
| 7,762,984 B2 | 7/2010 | Kumoyama et al. |
| 7,810,395 B2 | 10/2010 | Zhou |
| 7,850,685 B2 | 12/2010 | Kunis et al. |
| 7,867,178 B2 | 1/2011 | Simnacher |
| 7,909,797 B2 | 3/2011 | Kennedy, II et al. |
| 7,942,850 B2 | 5/2011 | Levit et al. |
| 7,967,781 B2 | 6/2011 | Simpson et al. |
| 7,972,299 B2 | 7/2011 | Carter |
| 7,985,189 B1 | 7/2011 | Ogden et al. |
| 8,021,328 B2 | 9/2011 | Lee |
| 8,029,473 B2 | 10/2011 | Carter |
| 8,043,256 B2 | 10/2011 | Hansen |
| 8,066,732 B2 | 11/2011 | Paul et al. |
| 8,088,121 B2 | 1/2012 | Nishide |
| 8,157,760 B2 | 4/2012 | Criado et al. |
| 8,162,859 B2 | 4/2012 | Schultheiss et al. |
| 8,166,825 B2 | 5/2012 | Zhou |
| 8,192,368 B2 | 6/2012 | Woodruff |
| 8,197,505 B2 | 6/2012 | Hirszowicz et al. |
| 8,246,643 B2 | 8/2012 | Nita |
| 8,267,886 B2 | 9/2012 | Ewing |
| 8,292,913 B2 | 10/2012 | Warnack |
| 8,328,820 B2 | 12/2012 | Diamant |
| 8,364,235 B2 | 1/2013 | Kordis et al. |
| 8,372,034 B2 | 2/2013 | Levit |
| 8,382,738 B2 | 2/2013 | Simpson et al. |
| 8,414,527 B2 | 4/2013 | Mallaby |
| 8,419,613 B2 | 4/2013 | Saadat |
| 8,439,890 B2 | 5/2013 | Beyar |
| 8,556,813 B2 | 10/2013 | Cashman et al. |
| 8,556,851 B2 | 10/2013 | Hirszowicz |
| 8,574,247 B2 | 11/2013 | Adams et al. |

(56)        References Cited

U.S. PATENT DOCUMENTS

| | | | |
|---|---|---|---|
| 8,657,814 B2 | 2/2014 | Werneth |
| 8,709,075 B2 | 4/2014 | Adams et al. |
| 8,728,091 B2 | 5/2014 | Hakala et al. |
| 8,734,424 B2 | 5/2014 | Watanabe |
| 8,747,416 B2 | 6/2014 | Hakala et al. |
| 8,784,362 B2 | 7/2014 | Boutilette |
| 8,834,510 B2 | 9/2014 | Wilson et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 8,986,339 B2 | 3/2015 | Warnack |
| 8,992,519 B2 | 3/2015 | Kim et al. |
| 8,992,817 B2 | 3/2015 | Stamberg |
| 9,005,216 B2 | 4/2015 | Hakala et al. |
| 9,011,462 B2 | 4/2015 | Adams et al. |
| 9,011,463 B2 | 4/2015 | Adams et al. |
| 9,011,511 B2 | 4/2015 | Gregorich |
| 9,044,575 B2 | 6/2015 | Beasley et al. |
| 9,044,618 B2 | 6/2015 | Hawkins et al. |
| 9,044,619 B2 | 6/2015 | Hawkins et al. |
| 9,056,185 B2 | 6/2015 | Fischell et al. |
| 9,072,534 B2 | 7/2015 | Adams et al. |
| 9,089,669 B2 | 7/2015 | Haslinger et al. |
| 9,131,949 B2 | 9/2015 | Coleman et al. |
| 9,138,249 B2 | 9/2015 | Adams et al. |
| 9,138,260 B2 | 9/2015 | Miller et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,254,169 B2 | 2/2016 | Long et al. |
| 9,282,984 B2 | 3/2016 | Nita |
| 9,283,359 B2 | 3/2016 | Pepper |
| 9,289,132 B2 | 3/2016 | Ghaffari et al. |
| 9,289,224 B2 | 3/2016 | Adams et al. |
| 9,289,319 B2 | 3/2016 | Pacetti et al. |
| 9,320,530 B2 | 4/2016 | Grace |
| 9,333,000 B2 | 5/2016 | Hakala et al. |
| 9,339,632 B2 | 5/2016 | Eidenschink et al. |
| 9,364,645 B2 | 6/2016 | Erikawa |
| 9,375,223 B2 | 6/2016 | Wallace |
| 9,421,025 B2 | 8/2016 | Hawkins et al. |
| 9,433,428 B2 | 9/2016 | Hakala et al. |
| 9,433,745 B2 | 9/2016 | Cully |
| 9,504,809 B2 | 11/2016 | Bo |
| 9,510,887 B2 | 12/2016 | Burnett |
| 9,522,012 B2 | 12/2016 | Adams |
| 9,554,815 B2 | 1/2017 | Adams et al. |
| 9,555,267 B2 | 1/2017 | Ein-Gal |
| 9,566,209 B2 | 2/2017 | Katragadda et al. |
| 9,579,114 B2 | 2/2017 | Mantell et al. |
| 9,579,492 B2 | 2/2017 | Simpson |
| 9,585,684 B2 | 3/2017 | Nita et al. |
| 9,592,328 B2 | 3/2017 | Jeevanandam |
| 9,603,506 B2 | 3/2017 | Goldfarb et al. |
| 9,629,567 B2 | 4/2017 | Porath et al. |
| 9,642,673 B2 | 5/2017 | Adams |
| 9,662,069 B2 | 5/2017 | De Graff et al. |
| 9,687,166 B2 | 6/2017 | Subramaniam |
| 9,700,655 B2 | 7/2017 | Laudenslager et al. |
| 9,730,715 B2 | 8/2017 | Adams |
| 9,737,361 B2 | 8/2017 | Magana |
| 9,764,142 B2 | 9/2017 | Imran |
| 9,782,570 B2 | 10/2017 | Hirszowicz |
| 9,814,476 B2 | 11/2017 | Adams et al. |
| 9,833,348 B2 | 12/2017 | Jordan et al. |
| 9,839,764 B2 | 12/2017 | Chouinard |
| 9,861,377 B2 | 1/2018 | Mantell et al. |
| 9,867,629 B2 | 1/2018 | Hawkins et al. |
| 9,878,135 B2 | 1/2018 | Holzapfel et al. |
| 9,894,756 B2 | 2/2018 | Weinkam et al. |
| 9,901,704 B2 | 2/2018 | Appling |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |
| 10,039,561 B2 | 8/2018 | Adams et al. |
| 10,076,384 B2 | 9/2018 | Kasprzyk |
| 10,086,175 B2 | 10/2018 | Torres et al. |
| 10,124,153 B2 | 11/2018 | Feig |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,245,410 B2 | 4/2019 | Aggerholm |
| 10,327,846 B1 | 6/2019 | Stark et al. |
| 10,328,290 B2 | 6/2019 | Zhou et al. |
| 10,357,264 B2 | 7/2019 | Kat-Kuoy |
| 10,405,923 B2 | 9/2019 | Yu et al. |
| 10,406,031 B2 | 9/2019 | Thyzel |
| 10,406,318 B2 | 9/2019 | Williams |
| 10,420,569 B2 | 9/2019 | Adams |
| 10,439,791 B2 | 10/2019 | Kalhan |
| 10,441,300 B2 | 10/2019 | Hawkins |
| 10,449,339 B2 | 10/2019 | Wilson et al. |
| 10,463,430 B2 | 11/2019 | Dick |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,583,277 B2 | 3/2020 | Rundquist |
| 10,589,073 B2 | 3/2020 | Mallaby |
| 10,617,850 B2 | 4/2020 | Tal |
| 10,646,240 B2 | 5/2020 | Betelia et al. |
| 10,668,245 B2 | 6/2020 | Kanae |
| 10,682,178 B2 | 6/2020 | Adams et al. |
| 10,695,531 B2 | 6/2020 | Suzuki |
| 10,702,293 B2 | 7/2020 | Adams et al. |
| 10,709,462 B2 | 7/2020 | Nguyen et al. |
| 10,709,872 B2 | 7/2020 | Alvarez et al. |
| 10,758,255 B2 | 9/2020 | Adams |
| 10,797,684 B1 | 10/2020 | Benz et al. |
| 10,799,688 B2 | 10/2020 | Calhoun |
| 10,842,567 B2 | 11/2020 | Grace et al. |
| 10,850,075 B2 | 12/2020 | Tarunaga |
| 10,857,329 B2 | 12/2020 | Davies |
| 10,933,225 B2 | 3/2021 | Campbell |
| 10,952,740 B2 | 3/2021 | Dasnurkar et al. |
| 10,952,790 B2 | 3/2021 | Haverkost et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 10,974,028 B2 | 4/2021 | Buller et al. |
| 10,980,987 B2 | 4/2021 | Tarunaga |
| 11,000,299 B2 | 5/2021 | Hawkins et al. |
| 11,020,135 B1 | 6/2021 | Hawkins |
| 11,026,707 B2 | 6/2021 | Ku et al. |
| 11,040,176 B2 | 6/2021 | Blanchard et al. |
| 11,058,492 B2 | 7/2021 | Grace et al. |
| 11,076,874 B2 | 8/2021 | Hakala et al. |
| 11,116,939 B2 | 9/2021 | Jamous et al. |
| 11,141,131 B2 | 10/2021 | Stigall |
| 11,179,169 B2 | 11/2021 | Brouillete et al. |
| 11,207,493 B2 | 12/2021 | Suzuki et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 11,253,681 B2 | 2/2022 | Williams |
| 11,266,817 B2 | 3/2022 | Cope et al. |
| 11,389,171 B2 | 7/2022 | Goldsmith |
| 11,389,628 B2 | 7/2022 | Spencer |
| 11,395,669 B2 | 7/2022 | O'Malley et al. |
| 11,399,862 B2 | 8/2022 | Massimini et al. |
| 11,406,452 B2 | 8/2022 | Efremkin |
| 11,406,799 B2 | 8/2022 | McEvaddy et al. |
| 11,484,327 B2 | 11/2022 | Anderson et al. |
| 11,540,848 B2 | 1/2023 | Cai et al. |
| 11,564,729 B2 | 1/2023 | Walzman |

(56)                References Cited

U.S. PATENT DOCUMENTS

| | | |
|---|---|---|
| 11,602,363 B2 | 3/2023 | Nguyen |
| 11,633,200 B2 | 4/2023 | Anderson et al. |
| 11,672,585 B2 | 6/2023 | Schultheis |
| 11,672,599 B2 | 6/2023 | Schultheis et al. |
| 11,707,323 B2 | 7/2023 | Schultheis et al. |
| 11,771,449 B2 | 10/2023 | Adams et al. |
| 11,779,363 B2 | 10/2023 | Vo |
| 11,826,530 B2 | 11/2023 | Suzuki |
| 11,839,391 B2 | 12/2023 | Schultheis et al. |
| 11,911,054 B2 | 2/2024 | Singla |
| 11,911,056 B2 | 2/2024 | Anderson et al. |
| 11,918,285 B2 | 3/2024 | Sun et al. |
| 11,944,331 B2 | 4/2024 | Anderson et al. |
| 11,950,793 B2 | 4/2024 | Nguyen |
| 12,011,185 B2 | 6/2024 | Vo |
| 12,023,098 B2 | 7/2024 | Nguyen |
| 12,035,932 B1 | 7/2024 | Nunes |
| 12,076,077 B2 | 9/2024 | Mori |
| 12,144,516 B2 | 11/2024 | Betelia |
| 12,178,458 B1 | 12/2024 | Betelia et al. |
| 12,193,691 B2 | 1/2025 | Adams |
| 2001/0016761 A1 | 8/2001 | Rudie |
| 2001/0018569 A1 | 8/2001 | Erbel |
| 2001/0020164 A1 | 9/2001 | Papademetriou |
| 2001/0049464 A1 | 12/2001 | Ganz |
| 2001/0051784 A1 | 12/2001 | Brisken |
| 2002/0045811 A1* | 4/2002 | Kittrell ............... G02B 6/4296 |
| | | 606/7 |
| 2002/0052621 A1 | 5/2002 | Fried et al. |
| 2002/0065512 A1 | 5/2002 | Fjield et al. |
| 2002/0082553 A1 | 6/2002 | Duchamp |
| 2002/0183620 A1 | 12/2002 | Tearney |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Evine et al. |
| 2003/0114901 A1 | 6/2003 | Loeb et al. |
| 2003/0125719 A1 | 7/2003 | Furnish |
| 2003/0144654 A1 | 7/2003 | Hilal |
| 2003/0176873 A1 | 9/2003 | Chernenko et al. |
| 2004/0002677 A1 | 1/2004 | Gentsler |
| 2004/0024349 A1 | 2/2004 | Flock et al. |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0210278 A1 | 10/2004 | Boll |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0142703 A1 | 6/2006 | Carter |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0027524 A1 | 2/2007 | Johnson |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142779 A1 | 6/2007 | Duane |
| 2007/0142819 A1 | 6/2007 | El-Nounou et al. |
| 2007/0142821 A1 | 6/2007 | Hennessy et al. |
| 2007/0142856 A1 | 6/2007 | Jang |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0033519 A1 | 2/2008 | Burwell |
| 2008/0081950 A1 | 4/2008 | Koenig et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0175539 A1 | 7/2008 | Brown |
| 2008/0195088 A1 | 8/2008 | Farr et al. |
| 2008/0214891 A1 | 9/2008 | Slenker et al. |
| 2008/0221550 A1 | 9/2008 | Lee |
| 2008/0281157 A1 | 11/2008 | Miyagi et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0131921 A1 | 5/2009 | Kurtz et al. |
| 2009/0192495 A1 | 7/2009 | Ostrovsky et al. |
| 2009/0240242 A1 | 9/2009 | Neuberger |
| 2009/0247945 A1 | 10/2009 | Levit |
| 2009/0281531 A1 | 11/2009 | Rizoiu |
| 2009/0292296 A1 | 11/2009 | Pansky |
| 2009/0296751 A1 | 12/2009 | Kewitsch et al. |
| 2009/0299327 A1 | 12/2009 | Tilson et al. |
| 2009/0306533 A1* | 12/2009 | Rousche .................. A61B 5/24 |
| | | 604/500 |
| 2009/0312768 A1 | 12/2009 | Hawkins et al. |
| 2010/0016862 A1 | 1/2010 | Hawkins et al. |
| 2010/0036238 A1 | 2/2010 | Neidert |
| 2010/0036294 A1 | 2/2010 | Mantell et al. |
| 2010/0063491 A1 | 3/2010 | Verhagen |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160838 A1 | 6/2010 | Krespi |
| 2010/0160903 A1 | 6/2010 | Krespi |
| 2010/0168572 A1 | 7/2010 | Sliwa |
| 2010/0168836 A1 | 7/2010 | Kassab |
| 2010/0168862 A1 | 7/2010 | Edie et al. |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2010/0265733 A1 | 10/2010 | O'Leary |
| 2010/0286791 A1 | 11/2010 | Goldsmith |
| 2010/0316333 A1 | 12/2010 | Luther |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1* | 10/2011 | Hastings ................ A61B 18/24 |
| | | 606/15 |

(56)            References Cited

U.S. PATENT DOCUMENTS

| | | |
|---|---|---|
| 2011/0263921 A1 | 10/2011 | Vrba et al. |
| 2011/0275990 A1 | 11/2011 | Besser et al. |
| 2011/0306956 A1 | 12/2011 | Islam |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0089132 A1 | 4/2012 | Dick et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0143131 A1 | 6/2012 | Tun |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0323211 A1 | 12/2012 | Ogle |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0060234 A1 | 3/2013 | Besser |
| 2013/0110003 A1 | 5/2013 | Surti |
| 2013/0116714 A1 | 5/2013 | Adams et al. |
| 2013/0165764 A1 | 6/2013 | Scheuermann |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0274726 A1 | 10/2013 | Takayama |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 2/2014 | Diodone et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0128848 A1 | 5/2014 | Appling et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1* | 8/2014 | Schmitt .................. A61B 18/24 |
| | | 606/15 |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0309536 A1 | 10/2014 | Douk et al. |
| 2014/0336626 A1 | 11/2014 | Jiang |
| 2014/0336632 A1 | 11/2014 | Toth |
| 2014/0336637 A1 | 11/2014 | Agrawal |
| 2014/0357997 A1 | 12/2014 | Hartmann |
| 2015/0003900 A1 | 1/2015 | Ullrich et al. |
| 2015/0005576 A1 | 1/2015 | Diodone et al. |
| 2015/0039002 A1 | 2/2015 | Hawkins |
| 2015/0057648 A1 | 2/2015 | Swift et al. |
| 2015/0071591 A1 | 3/2015 | Chen |
| 2015/0073430 A1 | 3/2015 | Hakala et al. |
| 2015/0080875 A1 | 3/2015 | Kasprzyk et al. |
| 2015/0105715 A1 | 4/2015 | Pikus et al. |
| 2015/0119870 A1 | 4/2015 | Rudie |
| 2015/0126990 A1 | 5/2015 | Sharma |
| 2015/0141764 A1 | 5/2015 | Harks et al. |
| 2015/0250542 A1 | 9/2015 | Islam |
| 2015/0276689 A1 | 10/2015 | Watanabe |
| 2015/0313732 A1 | 11/2015 | Fulton, III |
| 2015/0320432 A1 | 11/2015 | Adams |
| 2015/0342678 A1 | 12/2015 | Deladurantaye et al. |
| 2015/0342681 A1 | 12/2015 | Lee |
| 2015/0359432 A1 | 12/2015 | Ehrenreich |
| 2015/0359557 A1 | 12/2015 | Shimokawa |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0135891 A1 | 5/2016 | Feldman |
| 2016/0143522 A1* | 5/2016 | Ransbury ............. A61B 5/0071 |
| | | 600/116 |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184526 A1 | 6/2016 | Beyar |
| 2016/0184570 A1 | 6/2016 | Grace et al. |
| 2016/0228187 A1 | 8/2016 | Gross |
| 2016/0234534 A1 | 8/2016 | Kitahara et al. |
| 2016/0262784 A1 | 9/2016 | Grace et al. |
| 2016/0270806 A1 | 9/2016 | Wallace |
| 2016/0302762 A1 | 10/2016 | Stigall et al. |
| 2016/0324564 A1 | 11/2016 | Gerlach et al. |
| 2016/0331389 A1 | 11/2016 | Hakala et al. |
| 2016/0339204 A1 | 11/2016 | Williams |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0192242 A1 | 7/2017 | Laycock |
| 2017/0209050 A1 | 7/2017 | Fengler et al. |
| 2017/0265942 A1* | 9/2017 | Grace .................. A61B 18/245 |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0045897 A1 | 2/2018 | Chia |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 5/2018 | Thumpudi et al. |
| 2018/0169392 A1 | 6/2018 | Franklin |
| 2018/0214677 A1 | 8/2018 | Tarunaga |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0323571 A1 | 11/2018 | Brown et al. |
| 2018/0333043 A1 | 11/2018 | Teriluc |
| 2018/0360482 A1 | 12/2018 | Nguyen |
| 2019/0029702 A1 | 1/2019 | De Cicco |

(56) References Cited

U.S. PATENT DOCUMENTS

| | | |
|---|---|---|
| 2019/0029703 A1 | 1/2019 | Wasdyke et al. |
| 2019/0069916 A1 | 3/2019 | Hawkins et al. |
| 2019/0072378 A1 | 3/2019 | Hane et al. |
| 2019/0097380 A1 | 3/2019 | Luft et al. |
| 2019/0099588 A1 | 4/2019 | Ramanath et al. |
| 2019/0104933 A1 | 4/2019 | Stern |
| 2019/0117242 A1 | 4/2019 | Lawinger |
| 2019/0150960 A1 | 5/2019 | Nguyen et al. |
| 2019/0150961 A1 | 5/2019 | Tozzi |
| 2019/0159792 A1 | 5/2019 | Panian |
| 2019/0167349 A1 | 6/2019 | Shamay |
| 2019/0175111 A1 | 6/2019 | Genereux et al. |
| 2019/0175300 A1 | 6/2019 | Horn et al. |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0285803 A1 | 9/2019 | Van Zuylen |
| 2019/0321100 A1 | 10/2019 | Masotti et al. |
| 2019/0321101 A1 | 10/2019 | Massoti et al. |
| 2019/0328259 A1 | 10/2019 | Deno et al. |
| 2019/0365400 A1 | 12/2019 | Adams et al. |
| 2019/0380589 A1 | 12/2019 | Lloret |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1* | 12/2019 | Bhawalkar ............ A61B 5/742 |
| 2019/0388654 A1 | 12/2019 | Chou |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046429 A1 | 2/2020 | Tschida et al. |
| 2020/0046949 A1 | 2/2020 | Chisena et al. |
| 2020/0054352 A1 | 2/2020 | Brouillette et al. |
| 2020/0060814 A1 | 2/2020 | Murphy |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0101269 A1 | 4/2020 | Hayes |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0345380 A1 | 11/2020 | Boyle et al. |
| 2020/0383724 A1 | 12/2020 | Adams et al. |
| 2020/0397230 A1 | 12/2020 | Massimini et al. |
| 2020/0397453 A1 | 12/2020 | McGowan |
| 2020/0398033 A1 | 12/2020 | McGowan et al. |
| 2020/0405333 A1 | 12/2020 | Massimini et al. |
| 2020/0405391 A1 | 12/2020 | Massimini |
| 2020/0406009 A1 | 12/2020 | Massimini |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0116302 A1 | 4/2021 | Jean-Ruel |
| 2021/0128241 A1 | 5/2021 | Schultheis |
| 2021/0137598 A1 | 5/2021 | Cook et al. |
| 2021/0153939 A1 | 5/2021 | Cook |
| 2021/0177442 A1 | 6/2021 | Girdhar et al. |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0307828 A1 | 10/2021 | Schultheis |
| 2021/0330384 A1 | 10/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0378744 A1 | 12/2021 | Fanier et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0001138 A1 | 1/2022 | Howell |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0040454 A1 | 2/2022 | Hamm |
| 2022/0054194 A1 | 2/2022 | Bacher et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0249166 A1 | 8/2022 | Cook et al. |
| 2022/0273324 A1 | 9/2022 | Schultheis |
| 2022/0287732 A1 | 9/2022 | Anderson et al. |
| 2022/0313293 A1 | 10/2022 | Singh |
| 2022/0313359 A1 | 10/2022 | Schultheis et al. |
| 2022/0338890 A1 | 10/2022 | Anderson et al. |
| 2022/0354578 A1 | 11/2022 | Cook |
| 2022/0387106 A1 | 12/2022 | Cook |
| 2023/0013920 A1 | 1/2023 | Massimini |
| 2023/0064371 A1 | 3/2023 | Cook et al. |
| 2023/0137107 A1 | 5/2023 | Cook et al. |
| 2023/0157754 A1 | 5/2023 | Bacher et al. |
| 2023/0200906 A1 | 6/2023 | Cook et al. |
| 2023/0233256 A1 | 7/2023 | Cook et al. |
| 2023/0240748 A1 | 8/2023 | Cook et al. |
| 2023/0248376 A1 | 8/2023 | Anderson et al. |
| 2023/0255635 A1 | 8/2023 | Schultheis et al. |
| 2023/0255688 A1 | 8/2023 | Schultheis et al. |
| 2023/0255689 A1 | 8/2023 | Schultheis et al. |
| 2023/0310054 A1 | 10/2023 | Schultheis |
| 2023/0310067 A1 | 10/2023 | Schultheis et al. |
| 2023/0310073 A1 | 10/2023 | Adams et al. |
| 2023/0320576 A1 | 10/2023 | Feldman |
| 2023/0338088 A1 | 10/2023 | Massimini et al. |
| 2023/0338089 A1 | 10/2023 | Schultheis |
| 2023/0414234 A1 | 12/2023 | Anderson et al. |
| 2024/0001076 A1 | 1/2024 | Gelsinger |
| 2024/0016508 A1 | 1/2024 | Kocur |
| 2024/0016544 A1 | 1/2024 | Schultheis et al. |
| 2024/0016545 A1 | 1/2024 | Schultheis et al. |
| 2024/0023813 A1 | 1/2024 | Milner |
| 2024/0032995 A1 | 2/2024 | Schultheis et al. |
| 2024/0033002 A1 | 2/2024 | Cook |
| 2024/0041520 A1 | 2/2024 | Schultheis et al. |
| 2024/0050170 A1 | 2/2024 | Fournier |
| 2024/0050696 A1 | 2/2024 | Japuntich |

(56) References Cited

U.S. PATENT DOCUMENTS

| | | |
|---|---|---|
| 2024/0058060 A1 | 2/2024 | Cook |
| 2024/0065711 A1 | 2/2024 | Hendrickson |
| 2024/0065712 A1 | 2/2024 | Schultheis |
| 2024/0099773 A1 | 3/2024 | Schabert |
| 2024/0122648 A1 | 4/2024 | Cook |
| 2024/0165658 A1 | 5/2024 | Fu |
| 2024/0173044 A1 | 5/2024 | Chen et al. |
| 2024/0173526 A1 | 5/2024 | Kofidis |
| 2024/0189543 A1 | 6/2024 | Salinas |
| 2024/0216062 A1 | 7/2024 | Cook |
| 2024/0260981 A1 | 8/2024 | Betelia |
| 2024/0260982 A1 | 8/2024 | Peterson |
| 2024/0277410 A1 | 8/2024 | Cook |
| 2024/0277974 A1 | 8/2024 | Oehler |
| 2024/0277980 A1 | 8/2024 | O'Neill |
| 2024/0285296 A1 | 8/2024 | Vo |
| 2024/0285922 A1 | 8/2024 | Chu |
| 2024/0299051 A1 | 9/2024 | Sidhu et al. |
| 2024/0307119 A1 | 9/2024 | Nguyen |
| 2024/0325045 A1 | 10/2024 | Otake |
| 2024/0382258 A1 | 11/2024 | Schultheis |
| 2025/0025237 A1 | 1/2025 | Cook |
| 2025/0040947 A1 | 2/2025 | Schultheis |

FOREIGN PATENT DOCUMENTS

| | | |
|---|---|---|
| AU | 2022227829 | 9/2022 |
| CA | 2229806 | 3/1997 |
| CA | 2281519 | 8/1998 |
| CA | 2983655 | 10/2016 |
| CA | 3209797 | 9/2022 |
| CN | 102057422 | 5/2011 |
| CN | 109223100 | 1/2019 |
| CN | 110638501 | 1/2020 |
| CN | 110638501 A | 1/2020 |
| CN | 106794043 | 3/2020 |
| CN | 11399346 | 1/2022 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| CN | 114053552 | 2/2022 |
| CN | 115175625 | 10/2022 |
| CN | 117752412 | 3/2024 |
| CN | 118055734 | 5/2024 |
| DE | 3038445 A1 | 5/1982 |
| DE | 3836337 A | 4/1990 |
| DE | 3913027 A1 | 10/1990 |
| DE | 69431758 | 1/2003 |
| DE | 10230626 | 1/2004 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 0547146 | 7/1995 |
| EP | 1179993 A1 | 2/2002 |
| EP | 1946712 | 7/2008 |
| EP | 1946712 A1 | 7/2008 |
| EP | 1453566 | 9/2008 |
| EP | 2157569 | 2/2010 |
| EP | 2470248 | 7/2012 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3266487 | 1/2018 |
| EP | 3318204 | 5/2018 |
| EP | 2879607 | 2/2019 |
| EP | 3461438 A1 | 4/2019 |
| EP | 3473195 A1 | 4/2019 |
| EP | 2961463 | 5/2019 |
| EP | 3240603 | 5/2019 |
| EP | 3197381 | 3/2020 |
| EP | 3643260 A1 | 4/2020 |
| EP | 3240494 | 3/2021 |
| EP | 3522812 | 12/2021 |
| EP | 3076881 B1 | 1/2022 |
| EP | 3932342 | 1/2022 |
| EP | 3936140 | 1/2022 |
| EP | 3960099 | 3/2022 |
| EP | 4051154 | 9/2022 |
| EP | 4129213 | 2/2023 |
| EP | 4277537 | 11/2023 |
| EP | 4297669 | 1/2024 |
| EP | 4146322 | 4/2024 |
| EP | 3182931 | 6/2024 |
| EP | 3950036 | 8/2024 |
| EP | 4034005 | 12/2024 |
| GB | 1082397 | 9/1967 |
| JP | S62275446 A | 11/1987 |
| JP | H05264763 | 10/1993 |
| JP | 1996089511 | 4/1996 |
| JP | H09117407 | 5/1997 |
| JP | 2001520070 | 10/2001 |
| JP | 2004519296 | 7/2004 |
| JP | 2008506447 | 3/2008 |
| JP | 2008083273 | 4/2008 |
| JP | 2009519777 | 5/2009 |
| JP | 2009213589 | 9/2009 |
| JP | 2011524203 | 9/2011 |
| JP | 4805208 | 11/2011 |
| JP | 4808620 | 11/2011 |
| JP | 2012505050 | 3/2012 |
| JP | 2014123147 | 7/2014 |
| JP | A2014516614 | 7/2014 |
| JP | A2015522344 | 8/2015 |
| JP | 2015217215 | 12/2015 |
| JP | 2018538077 | 12/2018 |
| JP | 2024511710 | 3/2024 |
| KR | 20050098932 | 10/2005 |
| KR | 20080040111 | 5/2008 |
| KR | 20160090877 A | 8/2016 |
| KR | 20180054041 | 5/2018 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | WO9524867 | 9/1995 |
| WO | 9902095 A1 | 1/1999 |
| WO | 1999002095 A1 | 1/1999 |
| WO | 9920189 A1 | 4/1999 |
| WO | 1999020189 A1 | 4/1999 |
| WO | WO200067648 | 11/2000 |
| WO | WO2000067648 A1 | 11/2000 |
| WO | WO0103599 | 1/2001 |
| WO | WO0103599 A2 | 1/2001 |
| WO | 20060006169 A2 | 1/2006 |
| WO | WO2006006169 | 1/2006 |

(56) References Cited

FOREIGN PATENT DOCUMENTS

| WO | WO2009121017 | | 10/2009 |
|----|----|----|----|
| WO | WO2009149321 | A1 | 12/2009 |
| WO | WO2009152352 | A2 | 12/2009 |
| WO | 2010042653 | A1 | 4/2010 |
| WO | WO2011094379 | | 8/2011 |
| WO | 20110126580 | A2 | 10/2011 |
| WO | WO2011126580 | A3 | 10/2011 |
| WO | WO2012025833 | | 3/2012 |
| WO | WO2012042619 | | 4/2012 |
| WO | WO20120052924 | A1 | 4/2012 |
| WO | WO2012058156 | | 5/2012 |
| WO | WO2012099974 | A2 | 7/2012 |
| WO | WO20120120495 | A2 | 9/2012 |
| WO | WO2013119662 | | 8/2013 |
| WO | 20130169807 | A1 | 11/2013 |
| WO | WO2013169807 | | 11/2013 |
| WO | WO2014022436 | A1 | 2/2014 |
| WO | WO2014025397 | A1 | 2/2014 |
| WO | WO20140022867 | A1 | 2/2014 |
| WO | WO2014138582 | | 9/2014 |
| WO | WO2015056662 | | 4/2015 |
| WO | WO2015097251 | A2 | 7/2015 |
| WO | 20150177790 | A1 | 11/2015 |
| WO | WO2016014999 | | 1/2016 |
| WO | WO2016089683 | A1 | 6/2016 |
| WO | WO2016090175 | | 6/2016 |
| WO | WO2016098670 | | 6/2016 |
| WO | WO2016109739 | | 7/2016 |
| WO | WO2016143556 | | 9/2016 |
| WO | WO2016151595 | A1 | 9/2016 |
| WO | WO2017004432 | A1 | 1/2017 |
| WO | WO20170192869 | A1 | 11/2017 |
| WO | 20180022641 | A1 | 2/2018 |
| WO | WO2018022593 | A1 | 2/2018 |
| WO | WO2018083666 | | 5/2018 |
| WO | 20180175322 | A1 | 9/2018 |
| WO | WO2018175322 | | 9/2018 |
| WO | WO2018191013 | | 10/2018 |
| WO | WO2019200201 | A1 | 10/2019 |
| WO | WO2019215869 | A1 | 11/2019 |
| WO | WO2019222843 | | 11/2019 |
| WO | WO2020056031 | | 3/2020 |
| WO | WO20200086361 | A1 | 4/2020 |
| WO | WO2020089876 | A1 | 5/2020 |
| WO | WO2020157648 | | 8/2020 |
| WO | WO2020256898 | | 12/2020 |
| WO | WO2020256898 | A1 | 12/2020 |
| WO | WO2020256949 | | 12/2020 |
| WO | WO2020256949 | A1 | 12/2020 |
| WO | WO2020263469 | A1 | 12/2020 |
| WO | WO2020263685 | A1 | 12/2020 |
| WO | WO2020263687 | A1 | 12/2020 |
| WO | WO2020263688 | A1 | 12/2020 |
| WO | WO2020263689 | A1 | 12/2020 |
| WO | WO2021061451 | | 4/2021 |
| WO | WO2021067563 | | 4/2021 |
| WO | WO2021086571 | A1 | 5/2021 |
| WO | WO2021096922 | A1 | 5/2021 |
| WO | WO2021101766 | | 5/2021 |
| WO | WO2021101766 | A1 | 5/2021 |
| WO | WO2021126762 | A1 | 6/2021 |
| WO | WO2021162855 | A1 | 8/2021 |
| WO | WO2021173417 | A1 | 9/2021 |
| WO | WO2021183367 | A1 | 9/2021 |
| WO | WO2021183401 | A1 | 9/2021 |
| WO | WO2021188233 | A1 | 9/2021 |
| WO | WO2021202248 | A1 | 10/2021 |
| WO | WO2021231178 | A1 | 11/2021 |
| WO | WO2021247685 | A1 | 12/2021 |
| WO | WO2021257425 | A1 | 12/2021 |
| WO | WO2022007490 | | 1/2022 |
| WO | WO2022008440 | | 1/2022 |
| WO | WO2022010767 | A1 | 1/2022 |
| WO | WO2022055784 | | 3/2022 |
| WO | WO2022125525 | | 6/2022 |
| WO | WO2022154954 | | 7/2022 |
| WO | WO2022173719 | | 8/2022 |
| WO | WO2022183075 | | 9/2022 |
| WO | WO2022187058 | | 9/2022 |
| WO | WO2022216488 | | 10/2022 |
| WO | WO2022240674 | | 11/2022 |
| WO | WO2022260932 | | 12/2022 |
| WO | WO2023107334 | | 6/2023 |
| WO | WO2024079108 | | 4/2024 |
| WO | WO2024107418 | | 5/2024 |

OTHER PUBLICATIONS

International Search Report and Written Opinion dated Aug. 25, 2022 in PCT Application Serial No. PCTUS/2022/028035.

International Search Report and Written Opinion dated Sep. 15, 2022 in PCT Application Serial No. PCTUS/2022/032045.

Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.

Jones, H. M., et al. "Pulsed dielectric breakdown of pressurized water and salt solutions", Journal of Applied Physics, Jun. 1998, pp. 795-805, vol. 77, No. 2, American Institute of Physics.

Kozulin, I., et al. "The dynamic of the water explosive vaporization on the flat microheater", Journal of Physics: Conference Series, 2018, pp. 1-4, IOP Publishing, Russia.

Cross, F., "Laser Angioplasty", Vascular Medicine Review, 1992, pp. 21-30, Edward Arnold.

Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pps. 1156-1167, vol. 35, No. 8, IEEE.

Pratsos, A., "The use of Laser for the treatment of coronary artery disease", Bryn Mawr Hospital, 2010.

Li, Xian-Dong, et al. "Influence of deposited energy on shock wave induced by underwater pulsed current discharge", Physics of Plasmas, 2016, vol. 23, American Institute of Physics.

Logunov, S., et al. "Light diffusing optical fiber illumination", Renewable Energy and the Environment Congress, 2013, Corning, NY, USA.

Maxwell, A. D., et al. "Cavitation clouds created by shock scattering from bubbles during histotripsy", Acoustical Society of America, 2011, pp. 1888-1898, vol. 130, No. 4, Acoustical Society of America.

Mcateer, James A., et al. "Ultracal-30 Gypsum Artificial Stones for Research on the Mechinisms of Stone Breakage in Shock Wave Lithotripsy", 2005, pp. 429-434, Springer-Verlag.

Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.

Vogel, A., et al. "Mechanisms of Pulsed Laser Ablation of Biological Tissues", Chemical Reviews, 2003, pp. 577-644, vol. 103, No. 2, American Chemical Society.

Medlight, "Cylindrical light diffuser Model RD-ML", Medlight S.A., Switzerland.

Medlight, "Cylindircal light diffuser Model RD", Medlight S.A., Switzerland.

Mayo, Michael E., "Interaction of Laser Radiation with Urinary Calculi", Cranfield University Defense and Security, PhD Thesis, 2009, Cranfield University.

Vogel, A., et al. "Minimization of Cavitation Effects in Pulsed Laser Ablation Illustrated on Laser Angioplasty", Applied Physics, 1996, pp. 173-182, vol. 62, Springer-Verlag.

Mirshekari, G., et al. "Microscale Shock Tube", Journal of Microelectromechanical Systems, 2012, pp. 739-747, vol. 21, No. 3, IEEE.

"Polymicro Sculpted Silica Fiber Tips", Molex, 2013, Molex.

(56) References Cited

OTHER PUBLICATIONS

Zhou, J., et al. "Optical Fiber Tips and Their Applications", Polymicro Technologies a Subsidiary of Molex, Nov. 2007.

Liang, Xiao-Xuan, et al. "Multi-Rate-Equation modeling of the energy spectrum of laser-induced conduction band electrons in water", Optics Express, 2019, vol. 27, No. 4, Optical Society of America.

Nachabe, R., et al. "Diagnosis of breast cancer using diffuse optical spectroscopy from 500 to 1600 nm: comparison of classification methods", Journal of Biomedical Optics, 2011, vol. 16(8), SPIE.

Naugol'Nykh, K. A., et al. "Spark Discharges in Water", Academy of Sciences USSR Institute of Acoustics, 1971, Nauka Publishing Co., Moscow, USSR.

Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.

Nyame, Yaw A., et al. "Kidney Stone Models for in Vitro Lithotripsy Research: A Comprehensive Review", Journal of Endourology, Oct. 2015, pp. 1106-1109, vol. 29, No. 10, Mary Ann Liebert Inc., Cleveland, USA.

Ohl, Siew-Wan, et al. "Bubbles with shock waves and ultrasound: a review", Interface Focus, pp. 1-15, vol. 5, The Royal Society Publishing.

Zheng, W., "Optical Lenses Manufactured on Fiber Ends", IEEE, 2015, Splicer Engineering, Duncan SC USA.

Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.

"The New Optiguide DCYL700 Fiber Optic Diffuser Series", Optiguide Fiber Optic Spec Sheet, Pinnacle Biologics, 2014, Pinnacle Biologics, Illinois, USA.

Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.

Oshita, D., et al. "Characteristic of Cavitation Bubbles and Shock Waves Generated by Pulsed Electric Discharges with Different Voltages", IEEE, 2012, pp. 102-105, Kumamoto, Japan.

Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.

Murray, A., et al. "Peripheral laser angioplasty with pulsed dye laser and ball tipped optical fibres", The Lancet, 1989, pp. 1471-1474, vol. 2, Issue 8678-8679.

Mohammadzadeh, M., et al. "Photoacoustic Shock Wave Emission and Cavitation from Structured Optical Fiber Tips", Applied Physics Letters, 2016, vol. 108, American Institute of Physics Publishing LLC.

Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.

Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.

Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.

Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 898-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedical Optics, 2011, pp. 1-10, vol. 16, No. 1, SPIE.

Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissipation After Laser-induced Breakdown", SPIE, 1998, pp. 180-189, vol. 3254, SPIE.

International Search Report and Written Opinion, issued by the EP/ISA, in PCT/US2021/048819, dated Jan. 14, 2022.

Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.

Vogel, A., et al. "Acoustic transient generation by laser-produced cavitation bubbles near solid boundaries", Journal Acoustical Society of America, 1988, pp. 719-731, vol. 84.

Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.

Zheng, W., "Optic Lenses Manufactured on Fiber Ends", 2015, Splicer Engineering AFL, Duncan, SC USA.

Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.

Ali, Ziad A., et al. "Intravascular lithotripsy for treatment of stent underexpansion secondary to severe coronary calcification" 2018, European Society of Cardiology.

Ashok, Praveen C., et al. "Raman spectroscopy bio-sensor for tissue discrimination in surgical robotics—full article", Journal of Biophotonics, 2014, pp. 103-109, vol. 7, No. 1-2.

Ashok, Praveen C., et al. "Raman spectroscopy bio-sensor for tissue discrimination in surgical robotics—proof" Journal of Biophotonics 7, 2014, No. 1-2.

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

Bian, D. C., et al. "Study on Breakdown Delay Characteristics Based on High-voltage Pulse Discharge in Water with Hydrostatic Pressure", Journal of Power Technologies 97(2), 2017, pp. 89-102.

(56) References Cited

OTHER PUBLICATIONS

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.

Brodmann, Marianne et al. "Safety and Performance of Lithoplasty for Treatment of Calcified Peripheral Artery Lesions", JACC, 2017, vol. 70, No. 7.

Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.

"Bubble Dynamics and Shock Waves", Springer, 2013, Springer-Verlag, Berlin Heildelberg.

Hardy, Luke A., et al. "Cavitation Bubble Dynamics During Thulium Fiber Laser Lithotripsy", SPIE, Feb. 29, 2016, vol. 9689, San Francisco, California, USA.

Claverie, A., et al. "Experimental characterization of plasma formation and shockwave propagation induced by high power pulsed underwater electrical discharge", Review of Scientific Instruments, 2014, American Institute of Physics.

Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and on Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method for Fabricating Artificial Kidney Stones of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

International Search Report and Written Opinion dated Jun. 2, 2021 in PCT Application Serial No. PCT/US2021/018522.

International Search Report and Written Opinion dated Jun. 2, 2021 in PCT Application Serial No. PCT/US2021/015204.

International Search Report and Written Opinion dated Jun. 17, 2021 in PCT Application Serial No. PCT/US2021/020934.

International Search Report and Written Opinion dated Jul. 13, 2021 in PCT Application Serial No. PCT/US2021/024216.

International Search Report and Written Opinion dated Jun. 22, 2021 in PCT Application Serial No. PCT/US2021/020937.

International Search Report and Written Opinion dated Jun. 24, 2021 in PCT Application Serial No. PCT/US2021/021272.

International Search Report and Written Opinion dated Apr. 4, 2022 in PCT Application Serial No. PCT/US2021/062170.

(56)     References Cited

OTHER PUBLICATIONS

International Search Report and Written Opinion dated Apr. 4, 2022 in PCT Application Serial No. PCT/US2021/065073.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
International Search Report and Written Opinion, issued by the European Patent Office for PCT/2021/XXX, dated Sep. 30, 2021.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery of Atrial Endocardial Potential Maps From Non-contact Electrode Data." Auckland Bioengineering Institute. (ID 1421).
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368).
Sacher et al., "Comparison of Manual Vs Automatic Annotation to Identify Abnormal Substrate for Scar Related VT Ablation." LIRYC Institute, Bordeaux University Hospital, France (ID 1336).
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
Medlight, "Cylindrical light diffuser Model RD-ML", Medlight S.A., Switzerland. 2015. (This reference was cited in a prior Information Disclosure Statement. However, the relevant date was missing. The date has now been added.).

Medlight, "Cylindircal light diffuser Model RD", Medlight S.A., Switzerland. 2015. (This reference was cited in a prior Information Disclosure Statement. However, the relevant date was missing. The date has now been added.).
Ohl, Siew-Wan, et al. "Bubbles with shock waves and ultrasound: a review", Interface Focus, pp. 1-15, vol. 5, The Royal Society Publishing. Oct. 2015. (This reference was cited in a prior Information Disclosure Statement. However, the relevant date was missing. The date has now been added.).
Schafter+Kirchhoff, Laser Beam Couplers series 60SMS for coupling into single-mode and polarization—maintaining fiber cables, Schafter+Kirchhoff, pp. 1-5, Germany. Dec. 2, 2021. (This reference was cited in a prior Information Disclosure Statement. However, the relevant date was missing. The date has now been added.).
Meng et al., "Accurate Recovery of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (Id 1368). Poster for conference in San Francisco, May 8-11, 2019. (This reference was cited in a prior Information Disclosure Statement. However, the relevant date was missing. The date has now been added.).
Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019. (This reference was cited in a prior Information Disclosure Statement. However, the relevant date was missing. The date has now been added.).
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds in Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.

(56) References Cited

OTHER PUBLICATIONS

Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.

Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.

Reichel, E., et al. "Laser-induced Shock Wave Lithotripsy with a Regenerative Energy Converter", Lasers in Medical Science, 1992, pp. 423-425, vol. 7, Bailliere Tindall.

Hardy, L., et al. "Cavitation Bubble Dynamics during Thulium Fiber Laser Lithotripsy", SPIE BiOS, 2016, vol. 9689, SPIE.

Deckelbaum, L., "Coronary Laser Angioplasty", Lasers in Surgery and Medicine, 1994, pp. 101-110, vol. 14, Wiley-Liss Inc., Conneticuit, USA.

Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.

Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.

Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.

Varghese, B., et al. "Influence of absorption induced thermal initiation pathway on irradiance threshold for laser induced breakdown", Biomedical Optics Express, 2015, vol. 6, No. 4, Optical Society of America.

Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.

International Search Report and Written Opinion dated Jun. 27, 2018, in PCT Application Serial No. PCT/US2018/027121.

International Search Report and Written Opinion dated Jul. 20, 2018, in PCT Application Serial No. PCT/US2018/027801.

International Search Report and Written Opinion dated Jul. 20, 2018, in PCT Application Serial No. PCT/US2018/027784.

European Search Report, for European Patent Application No. 18185152, mailed Dec. 13, 2018.

International Search Report and Written Opinion dated May 22, 2019, in PCT Application Serial No. PCT/US2019/022009.

International Search Report and Written Opinion dated May 29, 2019, in PCT Application Serial No. PCT/US2019/022016.

International Search Report and Written Opinion dated Jun. 22, 2018, in Application Serial No. NL2019807, issued by the European Patent Office.

Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.

Chen, Sung-Liang, "Review of Laser-Generated Ultrasound Transmitters and their Applications to All-Optical Ultrasound Transducers and Imaging", Appl. Sci. 2017, 7, 25.

Colchester, R., et al. "Laser-Generated ultrasound with optica fibres using functionalised carbon nanotube composite coatings", Appl. Phys. Lett., 2014, vol. 104, 173504, American Institute of Physics.

Poduval, R., et al. "Optical fiber ultrasound transmitter with electrospun carbon nanotube-polymer composite", Appl. Phys. Lett., 2017, vol. 110, 223701, American Institute of Physics.

Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.

Kim, J., et al. "Optical Fiber Laser-Generated-Focused-Ultrasound Transducers for Intravascular Therapies", IEEE, 2017.

Kang, H., et al. "Enhanced photocoagulation with catheter-based diffusing optical device", Journal of Biomedical Optics, 2012, vol. 17, Issue 11, 118001, SPIE.

International Search Report and Written Opinion dated Jan. 3, 2020, in PCT Application Serial No. PCT/US2019/056579.

Communication Pursuant to Article 94(3) EPC, for European Patent Application No. 18185152.8, mailed Jan. 16, 2019.

European Search Report, for European Patent Application No. 18185152.8, mailed Dec. 20, 2018.

International Search Report and Written Opinion dated Jul. 29, 2020 in PCT Application Serial No. PCT/US2020/034005.

International Search Report and Written Opinion dated Sep. 11, 2020 in PCT Application Serial No. PCT/US2020/038517.

International Search Report and Written Opinion dated Sep. 9, 2020 in PCT Application Serial No. PCT/US2020/038530.

International Search Report and Written Opinion dated Sep. 11, 2020 in PCT Application Serial No. PCT/US2020/038521.

International Search Report and Written Opinion dated Sep. 7, 2020 in PCT Application Serial No. PCT/US2020/034642.

International Search Report and Written Opinion, PCT Application Serial No. PCT/US2022/047751 issued Feb. 10, 2023, by the European Patent Office. (56PCT).

AccuCoat, "Beamsplitter: Divide, combine & conquer"; 2023.

Lin et al., "Photoacoustic imaging", Science Direct; 2021.

Zhou et al., "Photoacoustic Imaging with fiber optic technology: A review", Science Direct; 2020.

International Search Report and Written Opinion issued by the European Patent Office, for Serial No. PCT/US2022/053775, dated Apr. 21, 2023. (Re 45PCT).

International Search Report and Written Opinion issued by the European Patent Office, for Serial No. PCT/US2023/011497, dated Apr. 28, 2023. (Re 54PCT).

International Search Report and Written Opinion issued by the European Patent Office, for Serial No. PCT/US2023/012599, dated May 19, 2023. (Re 57PCT).

Shen, Yajie et al. "High-peak-power and narrow-linewidth Q-switched Ho: YAG laser in-band pumped at 1931 nm." Applied Physics Express 13.5 (2020): 052006. (Year 2020).

PathFinder Digital, "Free Space Optics vs. Fiber Optics", 2023.

International Search Report and Written Opinion, issued in Application Serial No. PCT/US2023/016152, dated Jul. 12, 2023.

Definition of ablation—NCI Dictionary of Cancer Terms—NCI, National Cancer Institute, p. 1 (Year:2025).

Daemen, J., Tovar Forero, M.N, "The Coronary Intravascular Lithotripsy System", ICR Journal, 2019; 14(3); 174-181.

Butt, N., Khalid, N., Shlofmitz, E., "Intravascular Lithotripsy"; NCBI Bookshelf. A service of the National Library of Medicine, National Institutes of Health; StatPearls Publishing, 2023.

"Custom Medical Skived Tubing", Duke Extrusion, 2025. https://www.dukeextrusion.com/tubing-options/skived-tubing.

* cited by examiner

OPTICAL ANALYZER ASSEMBLY AND METHOD FOR INTRAVASCULAR LITHOTRIPSY DEVICE

RELATED APPLICATION

This application claims priority on U.S. Provisional Application Ser. No. 62/991,394, filed on Mar. 18, 2020. As far as permitted, the contents of U.S. Provisional Application Ser. No. 62/991,394 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

The present invention is directed toward a catheter system for treating a treatment site within or adjacent to a vessel wall or a heart valve. In various embodiments, the catheter system includes a light source, a balloon, a light guide and an optical analyzer assembly. The light source generates light energy. The balloon is positionable substantially adjacent to the treatment site. The balloon has a balloon wall that defines a balloon interior that receives a balloon fluid. The light guide is configured to receive the light energy at a guide proximal end and guide the light energy in a first direction from the guide proximal end toward a guide distal end that is positioned within the balloon interior. The optical analyzer assembly is configured to optically analyze light energy from the light guide that moves in a second direction opposite from the first direction.

In some embodiments, the balloon fluid is provided to the balloon interior so that the balloon expands from a collapsed configuration to an expanded configuration.

Additionally, in certain embodiments, the light source generates pulses of light energy that are guided along the light guide into the balloon interior to induce plasma generation in the balloon fluid within the balloon interior. In some such embodiments, the catheter system further includes a plasma generator that is positioned at the guide distal end of the light guide, the plasma generator being configured to generate plasma in the balloon fluid within the balloon interior. Further, in such embodiments, the plasma generation can cause rapid bubble formation and impart pressure waves upon the balloon wall adjacent to the vascular lesion.

In such embodiments, the optical analyzer assembly can be configured to optically detect whether plasma generation has occurred in the balloon fluid within the balloon interior. Additionally, the optical analyzer assembly can further be configured to optically detect whether a lack of plasma generation has occurred in the balloon fluid within the balloon interior. Further, the optical analyzer assembly can also be configured to optically detect a failure of the light guide at any point along a length of the light guide from the guide proximal end to the guide distal end. In certain such embodiments, the optical analyzer assembly can also be configured to optically detect potential damage to the light guide at any point along a length of the light guide from the guide proximal end to the guide distal end. Moreover, in some such embodiments, the optical analyzer assembly is configured to automatically shut down operation of the catheter system upon optical detection of potential damage to the light guide.

In some embodiments, the guide distal end includes a distal light receiver that receives light energy through the light guide from the guide distal end to the guide proximal end as a returning energy beam. In certain such embodiments, the light energy that is received by the light guide from the guide distal end to the guide proximal end is emitted from the plasma that is generated in the balloon fluid within the balloon interior. Further, in some such embodiments, the light energy that is received by the light guide from the guide distal end to the guide proximal end via the distal light receiver is optically analyzed by the optical analyzer assembly.

In certain embodiments, the catheter system further includes a pulse generator that is coupled to the light source. The pulse generator is configured to trigger the light source to emit pulses of light energy that are guided along the light guide from the guide proximal end to the guide distal end. In such embodiments, the pulses of light energy can energize a plasma generator that is positioned at the guide distal end of the light guide, the plasma generator being configured to generate plasma in the balloon fluid within the balloon interior. Additionally, in certain such embodiments, light energy is guided back through the light guide to the guide proximal end as a returning energy beam. In such embodiments, the optical analyzer assembly is configured to optically analyze the returning energy beam to determine whether plasma generation has occurred in the balloon fluid within the balloon interior.

In some embodiments, the optical analyzer assembly includes a beamsplitter and a photodetector. The beamsplitter is configured to receive the returning energy beam and direct at least a portion of the returning energy beam onto the photodetector. Additionally, in certain embodiments, the catheter system further includes an optical element that is positioned along a beam path between the beamsplitter and the photodetector, the optical element being configured to couple the at least a portion of the returning energy beam onto the photodetector. Further, in some embodiments, the photodetector generates a signal based at least in part on visible light that is included with the at least a portion of the returning energy beam. Additionally, the signal from the photodetector can be amplified with an amplifier to provide an amplified signal, and the amplified signal can be directed to control electronics to determine an intensity of the plasma generation in the balloon fluid within the balloon interior. Still further, in some embodiments, the amplified signal is gated using a discriminator circuit. In such embodiments, the control electronics compare timing of the pulse of energy from the light source as triggered by the pulse generator with the timing of the amplified signal from the photodetector to determine when plasma generation occurred in the balloon fluid within the balloon interior.

Additionally, in other embodiments, the catheter system further includes a second light source that generates light energy as an interrogation beam. In such embodiments, the light guide is configured to receive the interrogation beam from the second light source at the guide proximal end and guide the interrogation beam from the second light source toward the guide distal end. In some such embodiments, the catheter system further includes a pulse generator that is coupled to the second light source, the pulse generator being configured to trigger the second light source to emit pulses of light energy as interrogation beams that are guided along the light guide from the guide proximal end to the guide distal end. Additionally, in certain such embodiments, the second light source is a visible light source.

Further, in certain embodiments, the catheter system further includes a plasma generator that is positioned at the guide distal end of the light guide. In such embodiments, the interrogation beam is one of scattered by and reflected by the plasma generator and is directed along the light guide from the guide distal end to the guide proximal end as a returned interrogation beam. In certain embodiments, the returned interrogation beam is optically analyzed by the optical analyzer assembly as emitted from the guide proximal end of the light guide. Additionally, in some embodiments, the optical analyzer assembly includes a beamsplitter and a photodetector, and the beamsplitter in configured to receive the returned interrogation beam and direct at least a portion of the returned interrogation beam onto the photodetector. Further, in certain such embodiments, the photodetector generates a signal based at least in part on the at least a portion of the returned interrogation beam. Additionally, the signal from the photodetector can be amplified with an amplifier to provide an amplified signal; and the amplified signal can be directed to control electronics to determine when plasma generation occurred in the balloon fluid within the balloon interior. Still further, the amplified signal can be gated using a discriminator circuit. In such embodiments, the control electronics can compare timing of the pulse of light energy from the second light source as triggered by the pulse generator with the timing of the amplified signal from the photodetector to determine when plasma generation occurred in the balloon fluid within the balloon interior.

In some embodiments, the light source includes a laser.

Additionally, in certain embodiments, the light source includes an infrared laser that emits light energy in the form of pulses of infrared light.

Further, in some embodiments, the light guide includes an optical fiber.

In certain applications, the present invention is further directed toward a method for treating a vascular lesion within or adjacent to a vessel wall, the method including the steps of generating light energy with a light source; positioning a balloon substantially adjacent to the vascular lesion, the balloon having a balloon wall that defines a balloon interior that receives a balloon fluid; receiving light energy from the light source with a light guide at a guide proximal end; guiding the light energy with the light guide from the guide proximal end toward a guide distal end and into the balloon interior; and optically analyzing light energy emitted from the guide proximal end of the light guide with an optical analyzer assembly.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will

Figure 1:
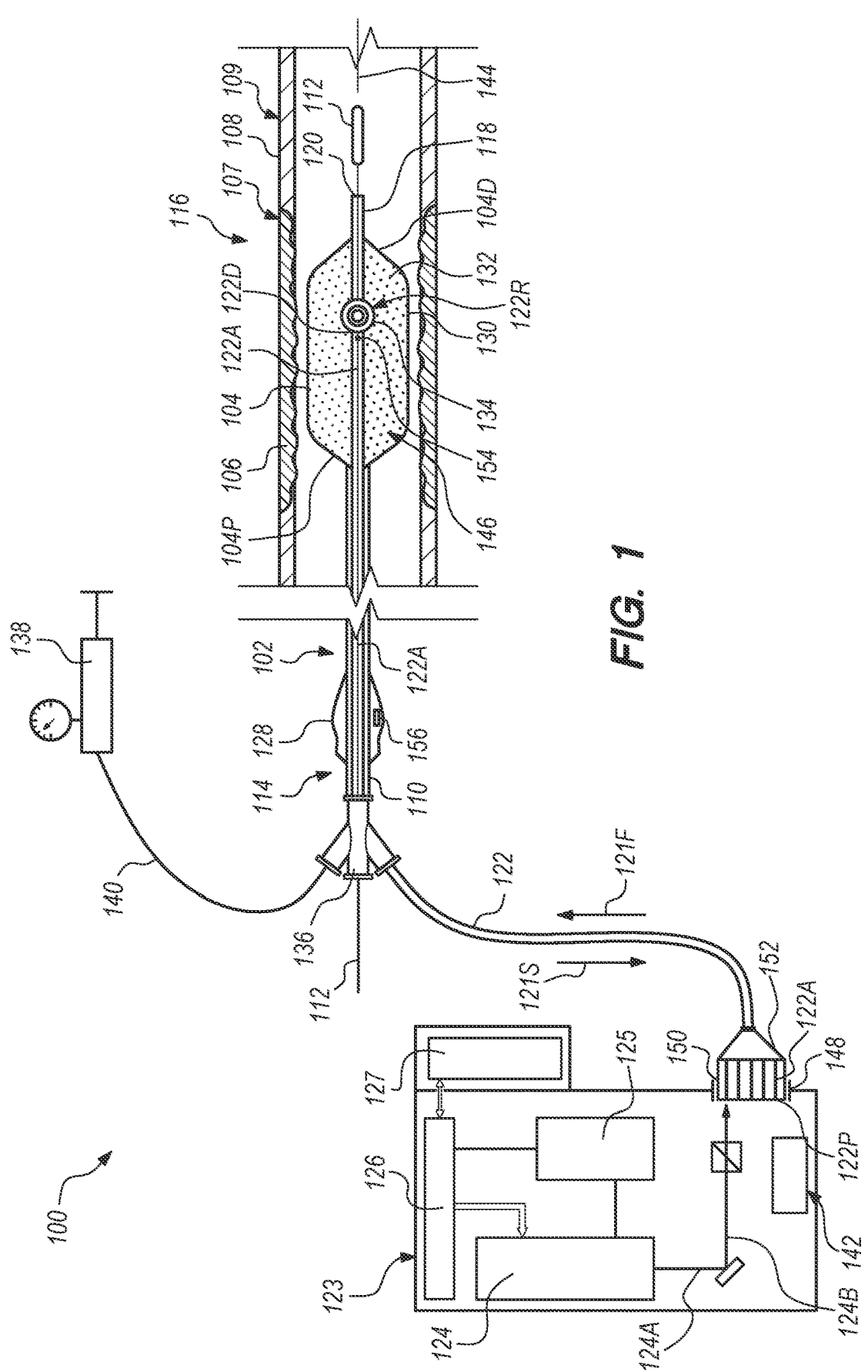
Figure 2:
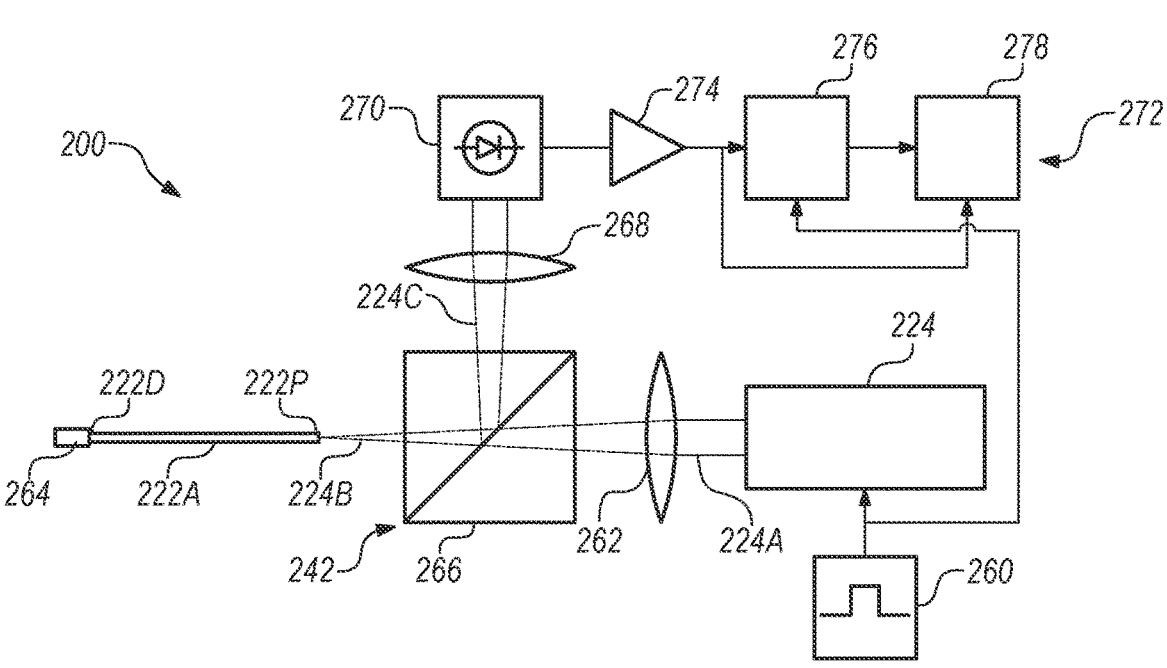
Figure 3:
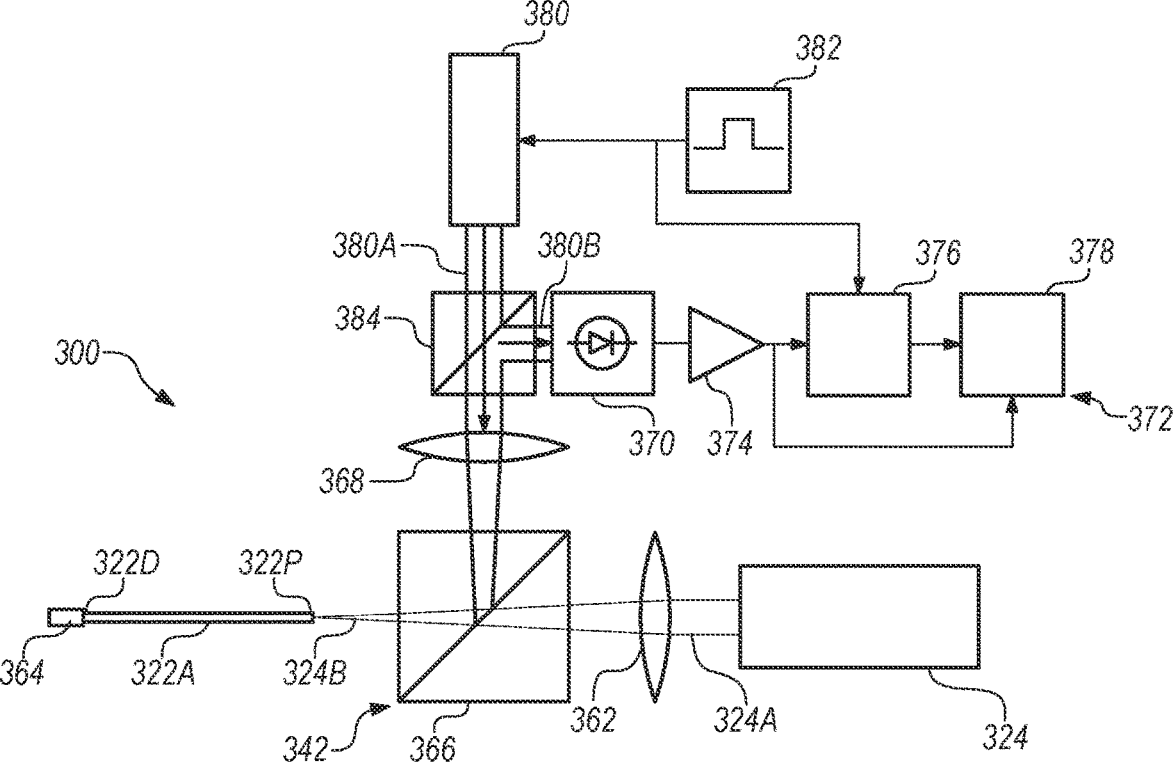

4 be best understood from the accompanying drawings, taken in conjunction with the accompanying description, in which similar reference characters refer to similar parts, and in which:

FIG. 1 is a schematic cross-sectional view of an embodiment of a catheter system in accordance with various embodiments herein, the catheter system including an optical analyzer assembly having features of the present invention;

FIG. 2 is a simplified schematic view of a portion of an embodiment of the catheter system including an embodiment of the optical analyzer assembly; and FIG. 3 is a simplified schematic view of a portion of another embodiment of the catheter system including another embodiment of the optical analyzer assembly.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions (also sometimes referred to herein as "treatment sites") can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

The catheter systems and related methods disclosed herein are configured to monitor the performance, reliability and safety of an intravascular lithotripsy (IVL) catheter. In various embodiments, the catheter systems of the present invention utilize an energy source, e.g., a light source such as a laser source or another suitable energy source, which provides energy that is guided by an energy guide, e.g., a light guide, to create a localized plasma in a balloon fluid within a balloon interior of an inflatable balloon of a catheter. As such, the energy guide can sometimes be referred to herein as, or can be said to incorporate a "plasma generator" at or near a guide distal end of the energy guide that is positioned within the balloon interior. This localized plasma induces pressure waves that impart pressure onto and induce fractures in a treatment site within or adjacent to a blood vessel wall within a body of a patient. As used herein, the treatment site can include a vascular lesion such as a calcified vascular lesion or a fibrous vascular lesion, typically found in a blood vessel and/or a heart valve.

In particular, in various embodiments, the catheter systems can include a catheter configured to advance to the treatment site within or adjacent a blood vessel or heart valve within the body of the patient. The catheter includes a catheter shaft, and a balloon that is coupled and/or secured to the catheter shaft. The balloons herein can include a balloon wall that defines the balloon interior and can be configured to receive the balloon fluid within the balloon interior to expand from a collapsed configuration suitable for advancing the catheter through a patient's vasculature, to an expanded configuration suitable for anchoring the catheter in position relative to the treatment site. The catheter systems also include one or more energy guides, e.g., light guides, disposed along the catheter shaft and within the balloon. Each energy guide can be configured for generating pressure waves within the balloon for disrupting the vascular lesions. The catheter systems utilize energy from an energy source, e.g., light energy from a light source, to generate the plasma, i.e. via the plasma generator, within the balloon fluid at or near a guide distal end of the energy guide disposed in the balloon located at the treatment site. The plasma formation can initiate one or more pressure waves and can initiate the rapid formation of one or more bubbles that can rapidly expand to a maximum size and then dissipate through a cavitation event that can launch pressure waves upon collapse. The rapid expansion of the plasma-induced bubbles can generate one or more pressure waves within the balloon fluid retained within the balloon and thereby impart pressure waves upon the treatment site. In some embodiments, the energy source can be configured to provide sub-millisecond pulses of energy, e.g., light energy, from the energy source to initiate plasma formation in the balloon fluid within the balloon to cause rapid bubble formation and to impart pressure waves upon the balloon wall at the treatment site. Thus, the pressure waves can transfer mechanical energy through an incompressible balloon fluid to the treatment site to impart a fracture force on the treatment site.

Importantly, as described in detail herein, the catheter systems of the present invention include an optical analyzer assembly that is configured to provide real-time continuous monitoring of the light emitted from the light guide into the balloon interior, which can be used to detect that a plasma event has occurred, and can also be used as a monitor for nominal operation of the catheter system. Additionally, the optical analyzer assembly can also be utilized to measure the intensity of the light energy emitted from the light guide in order to provide an accurate measurement of the energy output of the plasma generator that is incorporated as part of the light guide. More specifically, the measurement of the energy output of the plasma generator can be used in conjunction with the known energy input from the energy source to determine the conversion efficiency. Such metric can also be used to assess the condition of the plasma generator and light guide and determine if the catheter system is performing normally, as well as the number of operation cycles remaining.

More specifically, in various embodiments, as described in detail herein, the present invention comprises a means of sampling light returned from the plasma generator and/or from the balloon interior back through the light guide. It is appreciated that light energy can travel in both, opposing directions along the length of the light guide. Thus, it is possible to detect light originating at the guide distal end of the light guide, or at any other position along the length of the light guide, at a guide proximal end of the light guide. Such light energy that is transmitted back through the light guide will thus be separated and detected and/or analyzed via the optical analyzer assembly to effectively monitor the performance, reliability and safety of the catheter system as described in detail herein.

It is appreciated that the continuous monitoring of the light energy emitted from the plasma generator, and the measuring of the intensity of the emitted light energy, through use of the present invention, as described in detail herein, addresses multiple potential issues with the performance, reliability and safety of an IVL catheter, in particular one that utilizes an energy source to create a localized plasma which in turn produces a high energy bubble inside a balloon catheter. Specific issues this invention addresses include: 1) optical detection of successful firing of the energy source, e.g., the laser source, to generate the plasma within the balloon interior, 2) accurate determination of the energy output of the plasma generator, 3) optical detection of a failure of the catheter system to generate the desired plasma within the balloon interior, and 4) optical detection of a failure of the light guide at any point along the length of the light guide.

As used herein, the terms "intravascular lesion", "vascular lesion" and "treatment site" are used interchangeably unless otherwise noted. As such, the intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

It is appreciated that the catheter systems disclosed herein can include many different forms. Referring now to FIG. 1, a schematic cross-sectional view is shown of a catheter system 100 in accordance with various embodiments herein. As described herein, the catheter system 100 is suitable for imparting pressure to induce fractures in one or more vascular lesions within or adjacent a vessel wall of a blood vessel, or on or adjacent to a heart valve within a body of a patient. In the embodiment illustrated in FIG. 1, the catheter system 100 can include one or more of a catheter 102, a light guide bundle 122 including one or more light guides 122A, a source manifold 136, a fluid pump 138, a system console 123 including one or more of a light source 124, a power source 125, a system controller 126, and a graphic user interface 127 (a "GUI"), a handle assembly 128, and an optical analyzer assembly 142.

The catheter 102 is configured to move to a treatment site 106 within or adjacent to a blood vessel 108 within a body 107 of a patient 109. The treatment site 106 can include one or more vascular lesions such as calcified vascular lesions, for example. Additionally, or in the alternative, the treatment site 106 can include vascular lesions such as fibrous vascular lesions.

The catheter 102 can include an inflatable balloon 104 (sometimes referred to herein simply as a "balloon"), a catheter shaft 110 and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. The catheter shaft 110 can further include an inflation lumen (not shown). In some embodiments, the catheter 102 can have a distal end opening 120 and can accommodate and be tracked over the guidewire 112 as the catheter 102 is moved and positioned at or near the treatment site 106.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the balloon 104. In some embodiments, each light guide 122A can be an optical fiber and the light source 124 can be a laser. The light source 124 can be in optical communication with the light guides 122A at the proximal portion 114 of the catheter system 100.

In some embodiments, the catheter shaft 110 can be coupled to multiple light guides 122A such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110; or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, it is further appreciated that the light guides 122A described herein can be disposed uniformly or non-uniformly about the guidewire lumen 118 and/or the catheter shaft 110 to achieve the desired effect in the desired locations.

The balloon 104 can include a balloon wall 130 that defines a balloon interior 146, and can be inflated with a balloon fluid 132 to expand from a collapsed configuration suitable for advancing the catheter 102 through a patient's vasculature, to an expanded configuration suitable for anchoring the catheter 102 in position relative to the treatment site 106. Stated in another manner, when the balloon 104 is in the expanded configuration, the balloon wall 130 of the balloon 104 is configured to be positioned substantially adjacent to the treatment site 106, i.e. to the vascular lesion(s). In some embodiments, the light source 124 of the catheter system 100 can be configured to provide sub-millisecond pulses of light from the light source 124, along the light guides 122A, to a location within the balloon interior 146 of the balloon 104, thereby inducing plasma formation in the balloon fluid 132 within the balloon interior 146 of the balloon 104. The plasma formation causes rapid bubble formation, and imparts pressure waves upon the treatment site 106. Exemplary plasma-induced bubbles are shown as bubbles 134 in FIG. 1.

It is appreciated that although the catheter systems 100 illustrated herein are generally described as including a light source 124 and one or more light guides 122A, the catheter system 100 can alternatively include any suitable energy source and energy guides for purposes of generating the desired plasma in the balloon fluid 132 within the balloon interior 146.

The balloons 104 suitable for use in the catheter systems 100 described in detail herein include those that can be passed through the vasculature of a patient when in the collapsed configuration. In some embodiments, the balloons 104 herein are made from silicone. In other embodiments, the balloons 104 herein are made from polydimethylsiloxane (PDMS), polyurethane, polymers such as PEBAX™ material available from Arkema, which has a location at King of Prussia, Pennsylvania, USA, nylon, and the like. In some embodiments, the balloons 104 can include those having diameters ranging from one millimeter (mm) to 25 mm in diameter. In some embodiments, the balloons 104 can include those having diameters ranging from at least 1.5 mm to 12 mm in diameter. In some embodiments, the balloons 104 can include those having diameters ranging from at least one mm to five mm in diameter.

Additionally, in some embodiments, the balloons 104 herein can include those having a length ranging from at least five mm to 300 mm. More particularly, in some embodiments, the balloons 104 herein can include those having a length ranging from at least eight mm to 200 mm. It is appreciated that balloons 104 of greater length can be positioned adjacent to larger treatment sites 106, and, thus, may be usable for imparting pressure onto and inducing fractures in larger vascular lesions or multiple vascular lesions at precise locations within the treatment site 106.

Further, the balloons 104 herein can be inflated to inflation pressures of between approximately one atmosphere (atm) and 70 atm. In some embodiments, the balloons 104 herein can be inflated to inflation pressures of from at least 20 atm to 70 atm. In other embodiments, the balloons 104 herein can be inflated to inflation pressures of from at least six atm to 20 atm. In still other embodiments, the balloons 104 herein can be inflated to inflation pressures of from at least three atm to 20 atm. In yet other embodiments, the balloons 104 herein can be inflated to inflation pressures of from at least two atm to ten atm.

Still further, the balloons 104 herein can include those having various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloons 104 herein can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The balloon fluid 132 can be a liquid or a gas. Exemplary balloon fluids 132 suitable for use herein can include, but are not limited to one or more of water, saline, contrast medium, fluorocarbons, perfluorocarbons, gases, such as carbon dioxide, and the like. In some embodiments, the balloon fluids 132 described can be used as base inflation fluids. In some embodiments, the balloon fluids 132 include a mixture of saline to contrast medium in a volume ratio of 50:50. In other embodiments, the balloon fluids 132 include a mixture of saline to contrast medium in a volume ratio of 25:75. In still other embodiments, the balloon fluids 132 include a mixture of saline to contrast medium in a volume ratio of 75:25. Additionally, the balloon fluids 132 suitable for use herein can be tailored on the basis of composition, viscosity, and the like in order to manipulate the rate of travel of the pressure waves therein. In certain embodiments, the balloon fluids 132 suitable for use herein are biocompatible. A volume of balloon fluid 132 can be tailored by the chosen light source 124 and the type of balloon fluid 132 used.

In some embodiments, the contrast agents used in the contrast media herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

Additionally, the balloon fluids 132 herein can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Suitable absorptive agents can include those with absorption maxima along the spectrum from at least ten nm to 2.5 μm. Alternatively, the balloon fluids 132 can include those that include absorptive agents that can selectively absorb light in the mid-infrared region (e.g., at least 2.5 μm to 15 μm), or the far-infrared region (e.g., at least 15 μm to one mm) of the electromagnetic spectrum. In various embodiments, the absorptive agent can be those that have an absorption maximum matched with the emission maximum of the laser used in the catheter system. By way of non-limiting examples, various lasers described herein can include neodymium:yttrium-aluminum-garnet (Nd:YAG–emission maximum=1064 nm) lasers, holmium:YAG (Ho:YAG–emission maximum=2.1 μm) lasers, or erbium:YAG (Er:YAG–emission maximum=2.94 μm) lasers. In some embodiments, the absorptive agents used herein can be water soluble. In other embodiments, the absorptive agents used herein are not water soluble. In some embodiments, the absorptive agents used in the balloon fluids 132 herein can be tailored to match the peak emission of the light source 124. Various light sources 124 having emission wavelengths of at least ten nanometers to one millimeter are discussed elsewhere herein.

It is appreciated that the catheter system 100 and/or the light guide bundle 122 disclosed herein can include any number of light guides 122A in optical communication with the light source 124 at the proximal portion 114, and with the balloon fluid 132 within the balloon interior 146 of the balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than 30 light guides 122A.

The light guides 122A herein can include an optical fiber or flexible light pipe. The light guides 122A herein can be thin and flexible and can allow light signals to be sent with very little loss of strength. The light guides 122A herein can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide light along its length from a proximal portion, i.e. a guide proximal end 122P, to a distal portion, i.e. a guide distal end 122D, having at least one optical window (not shown) that is positioned within the balloon interior 146. The light guides 122A can create a light path as a portion of an optical network including the light source 124. The light path within the optical network allows light to travel from one part of the network to another. Both the optical fiber and the flexible light pipe can provide a light path within the optical networks herein.

As provided herein, the guide distal end 122D can further include and/or incorporate a distal light receiver 122R that enables light energy to be moved back into and through the light guide 122A from the guide distal end 122D to the guide proximal end 122P. Stated another way, the light energy can move in a first direction 121F along the light guide 122A that is generally from the guide proximal end 122P toward the guide distal end 122D of the light guide 122A. At least a portion of the light energy can also move in a second direction 121S along the light guide 122A that is substantially opposite the first direction 121F, i.e. from the guide distal end 122D toward the guide proximal end 122P of the light guide 122A. Moreover, as described in greater detail herein below, the light energy emitted from the guide proximal end 122P after being moved back through the light guide 122A (in the second direction 121S) can be separated and then optically detected, interrogated and/or analyzed through use of the optical analyzer assembly 142.

Further, the light guides 122A herein can assume many configurations about and/or relative to the catheter shaft 110 of the catheters 102 described herein. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A herein can be disposed within one or more light guide lumens within the catheter shaft 110.

Additionally, it is further appreciated that the light guides 122A can be disposed at any suitable positions about the circumference of the guidewire lumen 118 and/or the catheter shaft 110, and the guide distal end 122D of each of the light guides 122A can be disposed at any suitable longitudinal position relative to the length of the balloon 104 and/or relative to the length of the guidewire lumen 118.

Further, the light guides 122A herein can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. Additionally, in such embodiments, the photoacoustic transducers 154 can have a shape that corresponds with and/or conforms to the guide distal end 122D of the light guide 122A.

The photoacoustic transducer 154 is configured to convert light energy into an acoustic wave at or near the guide distal end 122D of the light guide 122A. It is appreciated that the direction of the acoustic wave can be tailored by changing an angle of the guide distal end 122D of the light guide 122A.

It is further appreciated that the photoacoustic transducers 154 disposed at the guide distal end 122D of the light guide 122A herein can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. It is also appreciated that the light guide 122A can further include additional photoacoustic transducers 154 disposed along one or more side surfaces of the length of the light guide 122A.

The light guides 122A described herein can further include one or more diverting features or "diverters" (not shown in FIG. 1) within the light guide 122A that are configured to direct light to exit the light guide 122A toward a side surface e.g., at or near the guide distal end 122D of the light guide 122A, and toward the balloon wall 130. A diverting feature can include any feature of the system herein that diverts light from the light guide 122A away from its axial path toward a side surface of the light guide 122A. Additionally, the light guides 122A can each include one or more light windows disposed along the longitudinal or axial surfaces of each light guide 122A and in optical communication with a diverting feature. Stated in another manner, the diverting features herein can be configured to direct light in the light guide 122A toward a side surface, e.g., at or near the guide distal end 122D, where the side surface is in optical communication with a light window. The light windows can include a portion of the light guide 122A that allows light to exit the light guide 122A from within the light guide 122A, such as a portion of the light guide 122A lacking a cladding material on or about the light guide 122A.

Examples of the diverting features suitable for use herein include a reflecting element, a refracting element, and a fiber diffuser. Additionally, the diverting features suitable for focusing light away from the tip of the light guides 122A herein can include, but are not to be limited to, those having a convex surface, a gradient-index (GRIN) lens, and a mirror focus lens. Upon contact with the diverting feature, the light is diverted within the light guide 122A to the photoacoustic transducer 154 that is in optical communication with a side surface of the light guide 122A. As noted, the photoacoustic transducer 154 then converts light energy into an acoustic wave that extends away from the side surface of the light guide 122A.

The source manifold 136 can be positioned at or near the proximal portion 114 of the catheter system 100. The source manifold 136 can include one or more proximal end openings that can receive the plurality of light guides 122A of the light guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132 as needed.

As noted above, in the embodiment illustrated in FIG. 1, the system console 123 includes one or more of the light source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the light source 124, the power source 125, the system controller 126, and the GUI 127 can be provided within the catheter system 100 without the specific need for the system console 123.

Further, as illustrated in FIG. 1, in certain embodiments, at least a portion of the optical analyzer assembly 142 can also be positioned substantially within the system console 123. Alternatively, components of the optical analyzer assembly 142 can be positioned in a different manner than what is specifically shown in FIG. 1.

Additionally, as shown, the system console 123, and the components included therewith, is operatively coupled to the catheter 102, the light guide bundle 122, and the remainder of the catheter system 100. For example, in some embodiments, as illustrated in FIG. 1, the system console 123 can include a console connection aperture 148 (also sometimes referred to generally as a "socket") by which the light guide bundle 122 is mechanically coupled to the system console 123. In such embodiments, the light guide bundle 122 can include a guide coupling housing 150 (also sometimes referred to generally as a "ferrule") that houses a portion, e.g., the guide proximal end 122P, of each of the light guides 122A. The guide coupling housing 150 is configured to fit and be selectively retained within the console connection aperture 148 to provide the desired mechanical coupling between the light guide bundle 122 and the system console 123.

Further, the light guide bundle 122 can also include a guide bundler 152 (or "shell") that brings each of the individual light guides 122A closer together so that the light guides 122A and/or the light guide bundle 122 can be in a more compact form as it extends with the catheter 102 into the blood vessel 108 during use of the catheter system 100.

As provided herein, the light source 124 can be selectively and/or alternatively coupled in optical communication with each of the light guides 122A, i.e. to the guide proximal end 122P of each of the light guides 122A, in the light guide bundle 122. In particular, the light source 124 is configured to generate light energy in the form of a source beam 124A, e.g., a pulsed source beam, that can be selectively and/or alternatively directed to and received by each of the light guides 122A in the light guide bundle 122 as an individual guide beam 124B. Alternatively, the catheter system 100 can include more than one light source 124. For example, in one non-exclusive alternative embodiment, the catheter system 100 can include a separate light source 124 for each of the light guides 122A in the light guide bundle 122.

The light source 124 can have any suitable design. In certain embodiments, as noted above, the light source 124 can be configured to provide sub-millisecond pulses of light from the light source 124 that are focused onto a small spot in order to couple it into the guide proximal end 122P of the light guide 122A. Such pulses of light energy are then directed along the light guides 122A to a location within the balloon 104, thereby inducing plasma formation in the balloon fluid 132 within the balloon interior 146 of the balloon 104. In particular, the light energy emitted at the guide distal end 122D of the light guide 122A energizes the plasma generator to form the plasma within the balloon fluid 132 within the balloon interior 146. The plasma formation causes rapid bubble formation, and imparts pressure waves upon the treatment site 106. In such embodiments, the sub-millisecond pulses of light from the light source 124 can be delivered to the treatment site 106 at a frequency of between approximately one hertz (Hz) and 5000 Hz. In some embodiments, the sub-millisecond pulses of light from the light source 124 can be delivered to the treatment site 106 at a frequency of between approximately 30 Hz and 1000 Hz. In other embodiments, the sub-millisecond pulses of light from the light source 124 can be delivered to the treatment site 106 at a frequency of between approximately ten Hz and 100 Hz. In yet other embodiments, the sub-millisecond pulses of light from the light source 124 can be delivered to the treatment site 106 at a frequency of between approximately one Hz and 30 Hz. Alternatively, the sub-millisecond pulses of light can be delivered to the treatment site 106 at a frequency that can be greater than 5000 Hz.

It is appreciated that although the light source 124 is typically utilized to provide pulses of light energy, the light source 124 can still be described as providing a single source beam 124A, i.e. a single pulsed source beam.

The light sources 124 suitable for use herein can include various types of light sources including lasers and lamps. For example, in certain non-exclusive embodiments, the light source 124 can be an infrared laser that emits light energy in the form of pulses of infrared light. Alternatively, as noted above, the light sources 124, as referred to herein, can include any suitable type of energy source.

Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid 132 of the catheters 102 described herein. In various embodiments, the pulse widths can include those falling within a range including from at least ten ns to 200 ns. In some embodiments, the pulse widths can include those falling within a range including from at least 20 ns to 100 ns. In other embodiments, the pulse widths can include those falling within a range including from at least one ns to 500 ns.

Additionally, exemplary nanosecond lasers can include those within the UV to IR spectrum, spanning wavelengths of about ten nanometers (nm) to one millimeter (mm). In some embodiments, the light sources 124 suitable for use in the catheter systems 100 herein can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter systems 100 disclosed herein can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In some embodiments, the catheter systems 100 herein can generate pressure waves having maximum pressures in the range of at least two MPa to 50 MPa. In other embodiments, the catheter systems 100 herein can generate pressure waves having maximum pressures in the range of at least two MPa to 30 MPa. In yet other embodiments, the catheter systems 100 herein can generate pressure waves having maximum pressures in the range of at least 15 MPa to 25 MPa.

The pressure waves described herein can be imparted upon the treatment site 106 from a distance within a range from at least 0.1 millimeters (mm) to 25 mm extending radially from the light guides 122A when the catheter 102 is placed at the treatment site 106. In some embodiments, the pressure waves can be imparted upon the treatment site 106 from a distance within a range from at least ten mm to 20 mm extending radially from the light guides 122A when the catheter 102 is placed at the treatment site 106. In other embodiments, the pressure waves can be imparted upon the treatment site 106 from a distance within a range from at least one mm to ten mm extending radially from the light guides 122A when the catheter 102 is placed at the treatment site 106. In yet other embodiments, the pressure waves can be imparted upon the treatment site 106 from a distance within a range from at least 1.5 mm to four mm extending radially from the light guides 122A when the catheter 102 is placed at the treatment site 106. In some embodiments, the pressure waves can be imparted upon the treatment site 106 from a range of at least two MPa to 30 MPa at a distance from 0.1 mm to ten mm. In some embodiments, the pressure waves can be imparted upon the treatment site 106 from a range of at least two MPa to 25 MPa at a distance from 0.1 mm to ten mm.

The power source 125 is electrically coupled to and is configured to provide necessary power to each of the light source 124, the system controller 126, the GUI 127, the handle assembly 128, and the optical analyzer assembly 142. The power source 125 can have any suitable design for such purposes.

As noted, the system controller 126 is electrically coupled to and receives power from the power source 125. Additionally, the system controller 126 is coupled to and is configured to control operation of each of the light source 124, the GUI 127 and the optical analyzer assembly 142. The system controller 126 can include one or more processors or circuits for purposes of controlling the operation of at least the light source 124, the GUI 127 and the optical analyzer assembly 142. For example, the system controller 126 can control the light source 124 for generating pulses of light energy as desired, e.g., at any desired firing rate. Additionally, the system controller 126 can control and/or operate in conjunction with the optical analyzer assembly 142 to effectively provide real-time continuous monitoring of the performance, reliability and safety of the catheter system 100.

Additionally, the system controller 126 can further be configured to control operation of other components of the catheter system 100, e.g., the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. Additionally, the GUI 127 is electrically connected to the system controller 126. With such design, the GUI 127 can be used by the user or operator to ensure that the catheter system 100 is employed as desired to impart pressure onto and induce fractures into the vascular lesions at the treatment site 106. Additionally, the GUI 127 can provide the user or operator with information that can be used before, during and after use of the catheter system 100. In one embodiment, the GUI 127 can provide static visual data and/or information to the user or operator.

In addition, or in the alternative, the GUI 127 can provide dynamic visual data and/or information to the user or operator, such as video data or any other data that changes over time, e.g., during use of the catheter system 100. Further, in various embodiments, the GUI 127 can include one or more colors, different sizes, varying brightness, etc., that may act as alerts to the user or operator. Additionally, or in the alternative, the GUI 127 can provide audio data or information to the user or operator. It is appreciated that the specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. Additionally, in this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the light source 124, the fluid pump 138, the GUI 127 and the optical analyzer assembly 142. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. Additionally, in some embodiments, the circuitry 156 can receive electrical signals or data from the optical analyzer assembly 142. Further, or in the alternative, the circuitry 156 can transmit such electrical signals or otherwise provide data to the system controller 126.

In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, e.g., within the system console 123. It is understood that the handle assembly 128 can include fewer or additional components than those specifically illustrated and described herein.

As an overview, and as provided in greater detail herein, the optical analyzer assembly 142 is configured to effectively monitor the performance, reliability and safety of the catheter system 100. During use of the catheter system 100, when the plasma initially forms in the balloon fluid 132 within the balloon interior, the plasma emits broad-spectrum electromagnetic radiation. Additionally, as noted above, at least a portion of the light energy emitted can reflect off of, or otherwise be received by, the distal light receiver 122R near the guide distal end 122D of the light guide 122A. Such portion of the light energy can thus travel back through the light guide 122A in the second direction 121S to the guide proximal end 122P where it can be separated and detected. The intensity and timing of the visible light pulse relative to the plasma-generating pulse from the light source 124 provides an indication that the plasma generator functioned, its energy output, and its functional condition. It is appreciated that visible light flashes may occur in other locations along the length of the light guide 122A if the light guide 122A is damaged or broken. Such additional light flashes will also be coupled into the light guide 122A and carried back in the second direction 121S to the guide proximal end 122P. The intensity and timing of these additional light pulses can indicate a damaged light guide 122A or plasma generator.

It is appreciated that the failure of an energy-driven plasma generator or associated light guide 122A, e.g., if the light guide 122A breaks or is damaged during the use of the catheter system 100, could lead to patient or operator harm resulting from the leaked energy. Potential harms include tissue burns and retinal damage. As noted above, in some embodiments, the energy source 124 is a laser that emits invisible infrared light, making visible detection by the operator impossible. Thus, if the optical analyzer assembly 142 indicates any such failures to have occurred, the procedure and energy delivery, e.g., laser energy delivery, must be stopped immediately to mitigate the associated risks to the patient and the operator. Stated in another manner, with the design of the optical analyzer assembly 142 described herein, the present invention detects any noted failures within the catheter system 100, e.g., breaking of, damage to, or failure of the light guide 122A and/or the plasma generator, and provides an indicator or signal that the system controller 126 can use to lock out the energy source 124. This provides a necessary safety interlock for a potentially hazardous condition in which the energy source 124 can leak out in an undesirable way. Moreover, the system controller 126 could be used to indicate to the surgeon, e.g., via the GUI 127, to halt the procedure and remove the catheter 102 from the patient 109 under treatment.

Additionally, it is further appreciated that the optical analyzer assembly 142 can have any suitable design for purposes of effectively monitoring the performance, reliability and safety of the catheter system 100. Certain non-exclusive examples of potential designs for the optical analyzer assembly 142 are described in detail herein below.

FIG. 2 is a simplified schematic view of a portion of an embodiment of the catheter system 200 including an embodiment of the optical analyzer assembly 242. The design of the catheter system 200 is substantially similar to the embodiments illustrated and described herein above. It is appreciated that various components of the catheter system 200, such as are shown in FIG. 1, are not illustrated in FIG. 2 for purposes of clarity and ease of illustration. However, it is appreciated that the catheter system 200 will likely include most, if not all, of such components.

As shown in FIG. 2, the catheter system 200 again includes an energy source 224 that is configured to generate light energy in the form of a source beam 224A, e.g., a pulsed source beam, that can be selectively and/or alternatively directed to and received by each light guide 222A (only one light guide is illustrated in FIG. 2) as an individual guide beam 224B. In one non-exclusive embodiment, the energy source 224 is an infrared laser source, and the light guide 222A is a small diameter, multimode optical fiber. In the embodiment illustrated in FIG. 2, a pulse generator 260 is coupled to the energy source 224. The pulse generator 260 is configured to trigger the energy source 224, which, thus, emits an energy pulse as the source beam 224A. In certain embodiments, the source beam 224A from the energy source 224 passes through an optical element 262, e.g., a focusing lens, that is configured to focus the source beam 224A as the individual guide beam 224B down onto a guide proximal end 222P of the light guide 222A, thereby coupling the pulse of infrared energy, i.e. the individual guide beam 224B, into the light guide 222A.

Subsequently, the pulse of infrared energy, i.e. the individual guide beam 224B, travels along and/or through the light guide 222A and energizes a plasma generator 264 that is positioned and/or incorporated at or near a guide distal end 222D of the light guide 222A. The plasma generator 264 utilizes the pulse of infrared energy to create a localized plasma in the balloon fluid 132 (illustrated in FIG. 1) within the balloon interior 146 (illustrated in FIG. 1) of the balloon 104 (illustrated in FIG. 1).

Upon creation of the plasma in the balloon fluid 132 within the balloon interior 146, in various embodiments, a pulse of broad-spectrum light energy emitted from the plasma is coupled back into the guide distal end 222D of the light guide 222A. Such pulse of broad-spectrum light energy then travels back along and/or through the light guide 222A from where it is emitted from the guide proximal end 222P of the light guide 222A, i.e. as a returning energy beam 224C.

As described in detail herein, the optical analyzer assembly 242 is configured to effectively monitor the performance, reliability and safety of the catheter system 200 by optically analyzing the light energy emitted from the guide proximal end 222P of the light guide 222A, e.g., the returning energy beam 224C. The design of the optical analyzer assembly 242 can be varied to suit the specific requirements of the catheter system 200. In particular, in the embodiment shown in FIG. 2, the optical analyzer assembly 242 includes one or more of a beamsplitter 266, an optical element 268, e.g., a coupling lens, a photodetector 270, and a signal conditioning and processing system 272. Additionally, as shown, the signal conditioning and processing system 272 can include one or more of an amplifier 274, a discriminator 276, and control electronics 278, which can include one or more processors or circuits. Alternatively, in other embodiments, the optical analyzer assembly 242 and/or the signal conditioning and processing system 272 can include more components or fewer components than what is specifically illustrated and described herein.

As shown, the beamsplitter 266, e.g., a dichroic beamsplitter, is positioned in the optical path of the energy source 224 and the guide proximal end 222P of the light guide 222A. In certain embodiments, the beamsplitter 266 is configured to pass light for wavelengths longer than those visible to the photodetector 270. This can be referred to as the cutoff wavelength. The beamsplitter 266 is further configured to reflect all light having a wavelength that is shorter than the cutoff wavelength. As illustrated in FIG. 2, the returning energy beam 224C that is emitted from the guide proximal end 222P of the light guide 222A is reflected off of the beamsplitter 266 and is coupled into the photodetector 270 using the optical element 268. More particularly, the optical element 268, e.g., a coupling lens, is positioned in the optical path of the returning energy beam 224C after it is reflected off of the beamsplitter 266, between the beamsplitter 266 and the photodetector 270. The optical element 268 effectively images the guide proximal end 222P of the light guide onto the photodetector 270, thereby coupling light energy emitted from the guide proximal end 222P of the light guide 222A, i.e. in the form of the returning energy beam 224C, onto the photodetector 270. With such design, the visible light emitted from the plasma formed at the guide distal end 222D of the light guide 222A is collected by the photodetector 270.

Additionally, in some embodiments, the photodetector 270 generates a signal that is based on the visible light emitted from the plasma formed at the guide distal end 222D of the light guide 222A that has been collected by the photodetector 270. As shown in FIG. 2, the signal from the photodetector 270 is then directed to the signal conditioning and processing system 272, where detection of and intensity evaluation of the plasma event are determined. In particular, in certain embodiments, the signal from the photodetector 270 is directed toward the amplifier 274 where the signal from the photodetector 270 is amplified. The amplified signal is thus utilized, e.g., within the control electronics 278, to determine the intensity of the plasma event that occurred in the balloon fluid 132 within the balloon interior 146.

Further, in certain embodiments, the pulse from the amplified photodetector signal is gated using the discriminator 276, e.g., a discriminator circuit, that is triggered by the pulse from the pulse generator 260. This information can then be used, e.g., within the control electronics 278, to determine when the plasma event occurred in the balloon fluid 132 within the balloon interior 146. More specifically, the control electronics 278 can compare the timing of the original pulse of energy from the energy source 224, as triggered by the pulse generator 260, with the timing of the amplified photodetector signal, as gated using the discriminator 276, to determine when the plasma event occurred in the balloon fluid 132 within the balloon interior 146.

In some embodiments, the control electronics 278 of the signal conditioning and processing system 272 can be included as part of the system controller 126 (illustrated in FIG. 1). Alternatively, the control electronics 278 of the signal conditioning and processing system 272 can be provided independently of the system controller 126 and can be in electrical communication with the system controller 126.

It is appreciated that there are numerous other configurations for the photodetector 270 and the signal conditioning and processing system 272 that are needed to detect and analyze the light pulse returning from the light guide 222A, i.e. the returning energy beam 224C. For example, in another embodiment, the photodetector 270 can be a spectrometer that provides intensity and wavelength information about the returning energy beam 224C. In such embodiment, this information can be used to generate a spectral signature to further identify specific conditions or events in the light guide 222A and/or the plasma generator 264. More particularly, the small quantities of material comprising the plasma generator 264 will be vaporized during its regular operation. These will produce a spectral line that would be distinct. It is further appreciated that this approach could further be used to differentiate between a functioning plasma generator 264 and a broken or damaged light guide 222A.

As described in detail herein, the primary mechanism for the present invention is direct detection of the light pulse created by the plasma event in the balloon fluid 132 within the balloon interior 146. The signal conditioning and processing system 278 can be utilized to indicate the intensity of the light pulse, its spectrum, and when it occurs relative to the input pulse from the energy source 224. This can be interpreted as follows:

1) The light pulse must occur after a time interval determined by the length of the light guide 222A and the duration of the input energy pulse from the energy source 224. If the detected light pulse has the correct intensity and occurs within a specific time window, it is an indication that the plasma generator 264 functioned correctly.

2) If no light pulse is detected at all, it is an indication of device failure.

3) If a smaller light pulse is detected that occurs too early relative to the energy pulse from the energy source 224, this would be an indication of a failure of the light guide 222A.

4) If the light pulse is detected as having a different spectrum or missing a spectral line or signature, this could be used to indicate a device failure.

FIG. 3 is a simplified schematic view of a portion of another embodiment of the catheter system 300 including another embodiment of the optical analyzer assembly 342. The design of the catheter system 300 is substantially similar to the embodiments illustrated and described herein above. It is appreciated that various components of the catheter system 300, such as are shown in FIG. 1, are not illustrated in FIG. 3 for purposes of clarity and ease of illustration. However, it is appreciated that the catheter system 300 will likely include most, if not all, of such components.

As shown in FIG. 3, the catheter system 300 again includes an energy source 324 that is configured to generate light energy in the form of a source beam 324A, e.g., a pulsed source beam, that can be selectively and/or alternatively directed to and received by each light guide 322A (only one light guide is illustrated in FIG. 3) as an individual guide beam 324B. In one non-exclusive embodiment, the energy source 324 is an infrared laser source, and the light guide 322A is a small diameter, multimode optical fiber. In certain embodiments, the energy source 324 can again be configured to provide sub-millisecond pulses of energy as the source beam 324A, which are then focused, e.g., with an optical element 362, onto a small spot in order to couple it as the individual guide beam 324B into the guide proximal end 322P of the light guide 322A.

Subsequently, the individual guide beam 324B travels along and/or through the light guide 322A and energizes a plasma generator 364 that is positioned and/or incorporated at or near a guide distal end 322D of the light guide 322A. The plasma generator 364 utilizes the pulse of infrared energy to create a localized plasma in the balloon fluid 132 (illustrated in FIG. 1) within the balloon interior 146 (illustrated in FIG. 1) of the balloon 104 (illustrated in FIG. 1).

As described in detail herein, the optical analyzer assembly 342 is again configured to effectively monitor the performance, reliability and safety of the catheter system 300, e.g., the light guide 322A and the plasma generator 364, through optical analysis of light energy emitted from the guide proximal end 322P of the light guide 322A. However, in the embodiment illustrated in FIG. 3, the optical analyzer assembly 342 has a different design than in the previous embodiments. More specifically, in this embodiment, rather than detecting and analyzing the light pulse emitted from the plasma or broken section of the light guide as the returning energy beam 224C (illustrated in FIG. 2), a separate, second energy source 380, e.g., a second light source, is used to interrogate the light guide 322A. This approach has similarities to Optical Time Domain Reflectometry (OTDR) which is used for detecting failures in long optical fiber transmission lines.

In particular, in the embodiment shown in FIG. 3, the optical analyzer assembly 342 includes one or more of the second energy source 380, a pulse generator 382, a beamsplitter 366, an optical element 368, e.g., a coupling lens, a second beamsplitter 384, a photodetector 370, and a signal conditioning and processing system 372. Additionally, as shown, the signal conditioning and processing system 372 can include one or more of an amplifier 374, a discriminator

376, and control electronics 378, which can include one or more processors or circuits. Alternatively, in other embodiments, the optical analyzer assembly 342 and/or the signal conditioning and processing system 372 can include more components or fewer components than what is specifically illustrated and described herein.

As shown in the embodiment illustrated in FIG. 3, the pulse generator 382 is coupled to the second energy source 380, with the pulse generator 382 being configured to trigger the second energy source 380, which, thus, emits an energy pulse as an interrogation beam 380A. In one non-exclusive embodiment, the second energy source 380 is a high-intensity, visible wavelength laser, and the pulse generator 382 is used to create a short, high-intensity pulse from the second energy source 380. The interrogation beam 380A is initially directed toward the second beamsplitter 384, which, as described herein, can be used to create separate source and return paths for the second energy source 380. In one embodiment, the second beamsplitter 384 is an ordinary beamsplitter that has a high reflection-to-transmission ratio. This allows a small, but sufficient amount of light energy to be coupled into the light guide 322A.

Additionally, in certain embodiments, the interrogation beam 380A from the second energy source 380 then passes through the optical element 368, and is redirected onto the guide proximal end 322P of the light guide 322A by the beamsplitter 366, e.g., a dichroic beamsplitter. The interrogation beam 380A then travels along and/or through the length of the light guide 322A. The interrogation beam 380A will be scattered or reflected by the plasma generator 364 at or near the guide distal end 322D of the light guide 322A and return to the guide proximal end 322P. The same optical path is then used to collect and detect the returned light pulse, i.e. a returned interrogation beam 380B.

As shown in FIG. 3, the returned interrogation beam 380B is optically analyzed using the optical analyzer assembly 342. More particularly, as shown, the beamsplitter 366 and the optical element 368 are again utilized to separate the light energy returning through the light guide 322A, i.e. the returned interrogation beam 380B, to be emitted from the guide proximal end 322P of the light guide 322A. Subsequently, the returned interrogation beam 380B is directed toward the second beamsplitter 384. As noted above, the second beamsplitter 384 can have a high reflection-to-transmission ratio, which allows collection and detection of a weak reflected pulse from the light guide 322A in the form of the returned interrogation beam 380B. Thus, the portion of the returned interrogation beam 380B that is reflected by the second beamsplitter 384 can be collected and coupled into the photodetector 370. With such design, the optical element 368 effectively images the guide proximal end 322P of the light guide onto the photodetector 370, thereby coupling light energy emitted from the guide proximal end 322P of the light guide 322A, i.e. in the form of the returned interrogation beam 380B, onto the photodetector 370.

Additionally, in some embodiments, the photodetector 370 generates a signal that is based on the portion of the returned interrogation beam 380B that has been collected by the photodetector 370. As shown in FIG. 3, the signal from the photodetector 370 is then directed to the signal conditioning and processing system 372, where detection of the plasma event is determined. In certain embodiments, the signal from the photodetector 370 is directed toward the amplifier 374 where the signal from the photodetector 370 is amplified. Further, in some embodiments, the pulse from the amplified photodetector signal is gated using the discriminator 276, e.g., a discriminator circuit, that is triggered by the pulse from the pulse generator 382. This information can then be used, e.g., within the control electronics 378, to determine when and if the plasma event occurred in the balloon fluid 132 within the balloon interior 146. More specifically, the control electronics 378 can compare the timing of the original pulse of energy from the second energy source 380, as triggered by the pulse generator 382, with the timing of the electronic pulse of the amplified photodetector signal, as gated using the discriminator 376, to indicate where along the light guide 322A the interrogating pulse was returned, i.e. as the returned interrogation beam 380B. This could be conditioned to determine whether the returned interrogation beam 380B was from the plasma generator 364, which would be a maximum time difference between trigger pulse and return pulse. Conversely, a shorter time interval between the trigger pulse and the return pulse would indicate the return was nearer to the guide proximal end 322P of the light guide 322A, which would indicate a failure or break in the light guide.

In some embodiments, the control electronics 378 of the signal conditioning and processing system 372 can be included as part of the system controller 126 (illustrated in FIG. 1). Alternatively, the control electronics 378 of the signal conditioning and processing system 372 can be provided independently of the system controller 126 and can be in electrical communication with the system controller 126.

As noted above, the optical analyzer assembly of the present invention addresses multiple potential issues with the performance, reliability and safety of an IVL catheter, in particular one that utilizes an energy source, e.g., a light source such as a laser source, to create a localized plasma which in turn induces a high energy bubble in the balloon fluid within the balloon interior of the balloon. For example, as noted above, issues that are addressed by the present invention include, but are not limited to: (1) optical detection of successful firing of the energy source and/or the plasma generator to generate the plasma within the balloon interior, (2) accurate determination of the energy output of the plasma generator, (3) optical detection of failure of the catheter system, e.g., the plasma generator, to generate the desired plasma within the balloon interior, and (4) optical detection of a failure of the light guide within the plasma generator, the balloon or along any section of the catheter shaft.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the detailed description provided herein. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a vessel wall or a heart valve, the catheter system being configured to use a balloon fluid, the catheter system comprising:

a light source that generates light energy;

a balloon that is positionable substantially adjacent to the treatment site, the balloon having a balloon wall that defines a balloon interior, the balloon interior being configured to receive the balloon fluid;

a light guide that is configured to receive the light energy from the light source at a guide proximal end and guide the light energy so that the light energy from the light source moves through the light guide in a first direction from the guide proximal end toward a guide distal end that is positioned within the balloon interior, the light energy from the light source that moves through the light guide in the first direction being configured to generate plasma in the balloon fluid within the balloon interior, the guide distal end of the light guide being in fluid communication with the balloon fluid in which the plasma is configured to be generated, the light guide being configured to subsequently guide a portion of the light energy from the light source that is configured to generate the plasma in the balloon fluid within the balloon interior back through the light guide from the guide distal end to the guide proximal end in a second direction that is opposite the first direction, the portion of the light energy that is guided back through the light guide in the second direction being emitted from the plasma that is generated in the balloon fluid within the balloon interior; and an optical analyzer assembly that is configured to optically analyze the portion of the light energy from the guide proximal end of the light guide that moved back through the light guide in the second direction.

2. The catheter system of claim 1 wherein the light source generates pulses of light energy that induce the plasma generation in the balloon fluid within the balloon interior.

3. The catheter system of claim 1 wherein the optical analyzer assembly is configured to optically detect a failure of the light guide at any point along a length of the light guide from the guide proximal end to the guide distal end.

4. The catheter system of claim 1 wherein the optical analyzer assembly is configured to optically detect damage to the light guide at any point along a length of the light guide from the guide proximal end to the guide distal end.

5. The catheter system of claim 4 wherein the optical analyzer assembly is configured to automatically shut down operation of the catheter system upon optical detection of damage to the light guide.

6. The catheter system of claim 1 wherein second light energy including the portion of the light energy from the energy source is guided back through the light guide in the second direction as a returning energy beam, the optical analyzer assembly being configured to optically analyze the returning energy beam to determine when the plasma generation occurred in the balloon fluid within the balloon interior.

7. The catheter system of claim 6 wherein the optical analyzer assembly includes a beamsplitter and a photodetector, the beamsplitter being configured to receive the returning energy beam and direct at least a portion of the returning energy beam to the photodetector.

8. The catheter system of claim 7 further comprising an optical element that is positioned along a beam path between the beamsplitter and the photodetector, the optical element being configured to couple the at least a portion of the returning energy beam onto the photodetector.

9. The catheter system of claim 7 wherein the photodetector generates a signal based at least in part on visible light that is included with the at least a portion of the returning energy beam.

10. The catheter system of claim 9 further comprising an amplifier and control electronics; and wherein the signal from the photodetector is amplified with the amplifier to provide an amplified signal that is directed to the control electronics to determine an intensity of the plasma generation within the balloon interior.

11. The catheter system of claim 10 wherein the amplified signal is gated using a discriminator circuit, the control electronics being configured to compare a timing of a pulse of light energy from the light source as triggered by a pulse generator with a timing of the amplified signal from the photodetector to determine when the plasma generation occurred within the balloon interior.

12. The catheter system of claim 1 wherein the light source includes a laser.

13. The catheter system of claim 1 wherein the light source includes an infrared laser that emits light energy in the form of pulses of infrared light.

14. The catheter system of claim 1 wherein the light guide includes an optical fiber.

15. The catheter system of claim 1 wherein the balloon has a drug eluting coating.

16. The catheter system of claim 1 wherein the balloon interior receives the balloon fluid so that the balloon is inflated with the balloon fluid to an expanded configuration; and wherein the plasma is generated in the balloon fluid that is used to inflate the balloon to the expanded configuration.

17. The catheter system of claim 1 wherein the portion of the light energy from the light source that moves back through the light guide from the guide distal end to the guide proximal end includes broad-spectrum light energy emitted from the plasma that is coupled back into the guide distal end of the light guide.

18. A catheter system for treating a treatment site within or adjacent to a vessel wall or a heart valve, the catheter system being configured to use a balloon fluid, the catheter system comprising:

a light source that generates light energy;

a balloon that is positionable substantially adjacent to the treatment site, the balloon having a balloon wall that defines a balloon interior, the balloon interior being configured to receive the balloon fluid to expand the balloon to an expanded configuration;

a light guide that is configured to receive the light energy from the light source at a guide proximal end and guide the light energy so that the light energy from the light source moves through the light guide in a first direction from the guide proximal end toward a guide distal end that is positioned within the balloon interior, the light energy from the light source that moves through the light guide in the first direction being configured to generate plasma in the balloon fluid within the balloon interior that has been used to expand the balloon to the expanded configuration, the light guide being configured to subsequently guide a portion of the light energy from the light source that is configured to generate the plasma in the balloon fluid within the balloon interior that has been used to expand the balloon to the expanded configuration back through the light guide from the guide distal end to the guide proximal end in a second direction that is opposite the first direction, the portion of the light energy that is guided back through the light guide in the second direction being emitted from the plasma that is generated in the balloon fluid within the balloon interior; and an optical analyzer assembly that is configured to optically analyze the portion of the light energy from the guide proximal end of the light guide that moved back through the light guide in the second direction.

19. The catheter system of claim 18, wherein the light source generates pulses of light energy; and wherein the light guide is configured to guide the pulses of light energy into the balloon interior to induce the plasma generation in the balloon fluid within the balloon interior that has been used to expand the balloon to the expanded configuration.

20. The catheter system of claim 18 further comprising a pulse generator that is coupled to the light source, the pulse generator triggering the light source to emit pulses of light energy that are guided along the light guide from the guide proximal end to the guide distal end, the pulses of light energy being emitted from the guide distal end of the light guide into the balloon fluid within the balloon interior to generate the plasma in the balloon fluid within the balloon interior that has been used to expand the balloon to the expanded configuration.

21. The catheter system of claim 18 wherein the light guide guides the portion of the light energy back through the light guide to the guide proximal end as a returning energy beam; and wherein the optical analyzer assembly optically analyzes the returning energy beam to determine when the plasma generation occurred in the balloon fluid within the balloon interior that has been used to expand the balloon to the expanded configuration.

22. The catheter system of claim 21 wherein the optical analyzer assembly includes a beamsplitter and a photodetector, the beamsplitter being configured to receive the returning energy beam and direct at least a portion of the returning energy beam onto the photodetector.

23. The catheter system of claim 18 wherein the light source includes a laser; and wherein the light guide includes an optical fiber.

24. The catheter system of claim 18 wherein the portion of the light energy from the light source that moves back through the light guide from the guide distal end to the guide proximal end including broad-spectrum light energy emitted from the plasma that is coupled back into the guide distal end of the light guide.

* * * * *